United States Patent
Head et al.

(10) Patent No.: US 6,362,204 B1
(45) Date of Patent: *Mar. 26, 2002

(54) PHENYLALANINE DERIVATIVES

(75) Inventors: John Clifford Head; Sarah Catherine Archibald, both of Maidenhead; Graham John Warrellow, Northwood; John Robert Porter, Chinnor, all of (GB)

(73) Assignee: Celltech Therapeutics, Ltd, Slough (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/317,081

(22) Filed: May 20, 1999

(30) Foreign Application Priority Data

May 22, 1998 (DE) ............................................. 9811159

(51) Int. Cl.⁷ ................. A61K 31/4439; A61K 31/426; C07D 417/12; C07D 277/06; A61P 29/00
(52) U.S. Cl. ....................... 514/342; 514/256; 514/354; 514/365; 514/423; 544/335; 546/268.7; 546/269.7; 546/316; 548/200; 548/537; 548/538
(58) Field of Search .................. 546/268.7, 316, 546/269.7; 548/200, 537, 538; 544/335; 514/342, 354, 365, 423, 256

(56) References Cited

U.S. PATENT DOCUMENTS

| | | | |
|---|---|---|---|
| 4,470,973 A | 9/1984 | Natarajan et al | 424/177 |
| 4,554,273 A | 11/1985 | Bayssat et al. | 514/221 |
| 4,762,881 A | * 8/1988 | Kauer | 525/54.11 |
| 4,987,132 A | 1/1991 | Mase et al. | 514/252 |
| 5,164,372 A | 11/1992 | Matsuo et al. | 514/19 |
| 5,227,490 A | 7/1993 | Hartman et al. | |
| 5,260,277 A | 11/1993 | McKenzie | 544/18 |
| 5,296,486 A | 3/1994 | Lazer et al. | 514/333 |
| 5,510,346 A | 4/1996 | Martin et al. | 514/221 |
| 5,698,691 A | 12/1997 | Yukimasa et al. | 540/490 |
| 5,773,646 A | 6/1998 | Michael et al. | |
| 6,093,696 A | 7/2000 | Head et al. | 514/19 |

FOREIGN PATENT DOCUMENTS

| | | |
|---|---|---|
| DE | 23 16 881 A | 10/1973 |
| DE | 28 37 264 A1 | 3/1979 |
| DE | 196 54 483 A | 1/1998 |
| EP | 3847 * | 9/1979 |
| EP | 0 031 104 A1 | 7/1981 |
| EP | 0 048 763 A1 | 4/1982 |
| EP | 0 144 230 A | 6/1985 |
| EP | 284632 * | 10/1988 |
| EP | 0 288 176 A | 10/1988 |
| EP | 0 322 068 A1 | 6/1989 |
| EP | 0 394 989 A2 | 10/1990 |
| EP | 0 498 268 A2 | 8/1992 |
| EP | 0 596 406 A1 | 5/1994 |
| EP | 0 710 657 A1 | 5/1996 |
| EP | 0 710 659 A1 | 5/1996 |

(List continued on next page.)

OTHER PUBLICATIONS

Azzouny, A.E., et al., "Synthesis of some N–substituted salicylamides structurally related to certain antimicrobials," *Pharmazie*, 1977, 32(6), 318–323 (abstract).

Badshah, A., et al., "Catalytic reduction of azlactones in alkaline media. Synthesis of amino acids," *J. of Organic Chemistry*, 1972, 37(18), 2916–2918.

Tous, G., et al., "O'–(Epoxyalkyl) tyrosines and (Epoxyalkyl) phenylalanine as irreversible inactivators of serine proteases: synthesis and inhibition mechanism," *J. of Medicinal Chemistry*, 1990, 33(6), 1620–1634.

Lobb, R.R., et al., "Small molecule antagonists of alpha4 integrins: novel drugs for asthma," *Exp. Opin, Invest. Drugs*, 1999, XP000885957, 8(7), 935–945.

Samanen, J., et al., "Vascular indications for integrin alpha V antagonists," *Current Pharm. Design.*, 1997, 3, 545–584.

Šavrda, J., "CIS–TRANS isomerism of N–Acyl derivatives of proline and its analogues, linear peptides with CIS peptide bonds," *Proc. 14ᵗʰ European Peptide Symposium*, Loffet, A. (ed.), 1976, 653–656.

Clausen, K., et al., "Studies on amino acids and peptides. II. Synthesis of protected endothiodipeptides," *J. Chem. Scr.*, 1982, 20(1–2), 14–18, doc. No. 97:163474 (abstract only, 1 page).

Frank, R., et al., "Extremely mild reagent for Boc deprotection," *J. Chem. Commun. (Cambridge)*, 1996, 22, 2509–2510, doc. No. 126:104395 (abstract only, 3 pages).

Kobayashi, A., et al., "Syntheses of 2–dialkylamino–4,–4–disubstituted 5 (4H)–thiazolones," *J. Yakugaku Zasshi*, 1970,90(11), 1377–1380, doc. No. 74:31713 (abstract only, 3 pages).

(List continued on next page.)

*Primary Examiner*—Evelyn Mei Huang
(74) *Attorney, Agent, or Firm*—Woodcock Washburn, LLP

(57) ABSTRACT

Phenylalanine derivatives of formula (1) are described:

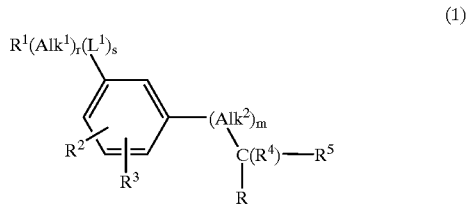

(1)

wherein
R is a carboxylic acid or a derivative thereof;
$L^1$ is a linker atom or group;
and $R^5$ is a group $-L^2(CH_2)_rR^6$ in which $L^2$ is a $-N(R^7)CO-$ or $-N(R^7)CS-$ group.

The compounds are able to inhibit the binding α4 integrins to their ligands and are of use in the prophylaxis and treatment of immune or inflammatory disorders.

9 Claims, No Drawings

FOREIGN PATENT DOCUMENTS

| | | |
|---|---|---|
| EP | 0 842 943 A2 | 5/1998 |
| EP | 0 842 945 A2 | 5/1998 |
| JP | 56 090045 | 7/1981 |
| JP | 63239256 | * 10/1988 |
| JP | 03 135962 | 6/1991 |
| WO | WO 86/02353 | 4/1986 |
| WO | WO 93/00095 | 1/1993 |
| WO | WO 93/08174 | 4/1993 |
| WO | WO 93/09795 | 5/1993 |
| WO | WO 94/15954 | 7/1994 |
| WO | WO 94/15955 | 7/1994 |
| WO | WO 94/29285 | 12/1994 |
| WO | 95/12611 | * 5/1995 |
| WO | WO 95/13811 | 5/1995 |
| WO | WO 95/15973 | 6/1995 |
| WO | WO 95/19356 | 7/1995 |
| WO | WO 95/35314 | 12/1995 |
| WO | WO 96/01644 | 1/1996 |
| WO | 96/18606 | * 6/1996 |
| WO | WO 96/22966 | 8/1996 |
| WO | WO 96/26190 | 8/1996 |
| WO | WO 97/03094 | 1/1997 |
| WO | WO 97/08145 | 3/1997 |
| WO | WO 97/12866 | 4/1997 |
| WO | WO 97/31907 | 9/1997 |
| WO | WO 97/36859 | 10/1997 |
| WO | 97/36862 | * 10/1997 |
| WO | WO 98/00395 | 1/1998 |
| WO | WO 98/04247 | 2/1998 |
| WO | WO 98/04913 | 2/1998 |
| WO | 98/17639 | * 4/1998 |
| WO | WO 98/42662 | 10/1998 |
| WO | WO 98/53814 | 12/1998 |
| WO | WO 98/53817 | 12/1998 |
| WO | WO 98/53818 | 12/1998 |
| WO | WO 98/54207 | 12/1998 |
| WO | WO 98/58902 | 12/1998 |
| WO | WO 99/06390 | 2/1999 |
| WO | WO 99/06431 | 2/1999 |
| WO | WO 99/06432 | 2/1999 |
| WO | WO 99/06433 | 2/1999 |
| WO | WO 99/06434 | 2/1999 |
| WO | WO 99/06435 | 2/1999 |
| WO | WO 99/06436 | 2/1999 |
| WO | WO 99/06437 | 2/1999 |
| WO | WO 99/10312 | 3/1999 |
| WO | WO 99/10313 | 3/1999 |
| WO | WO 99/20272 | 4/1999 |
| WO | WO 99/30709 | 6/1999 |
| WO | WO 99/35163 | 7/1999 |
| WO | WO 99/37618 | 7/1999 |
| WO | WO 99/43642 | 9/1999 |
| WO | WO 99/48879 | 9/1999 |
| WO | WO 99/61465 | 12/1999 |
| WO | WO 00/35855 | 6/2000 |

OTHER PUBLICATIONS

Koenig, H.B., et al., ".beta.–Lactam antibiotics," *Ger. Offen.*, 41 pages, doc. No. 83:97276 (abstract only, 5 pages).

Masuda, T., *Jpn. Kodai Tokkyo Koho*, 22 pages, doc. No. 115:280022 (abstract only, 1 page).

Pfeifer, T., et al., "Specific fragmentation of thioxo peptides facilitates the assignment of the thioxylated amino acid," *J. Mass Spectrom*, 1997, 32(10), 1064–1071, doc. No. 127:331738 (abstract only 2 pages).

Sawa, N., et al., "Preparation of 4(5)–thiocarbamoylimidazole compounds," *Jpn. Kokai Tokkyo Koho*, 33 pages, doc. No. 115:183296 (abstract only, 2 pages).

Schutkowski, M., et al., "Inhibition of peptidyl–prolyl cis/trans isomerase activity by substrate analog structures: thioxo tetrapeptide–4–nitroanilides," *Biochemistry*, 1995, 34(40), 13016–13026, doc. No. 123:221511 (abstract only, 4 pages).

"Cephalosporins," *Jpn. Kokai Tokkyo Koho*, 40 pages, doc. No. 99:5433 (abstract only, 2 pages).

Buckle, D.R., et al., "Non Thiazolidinedione Antihyperglycaemic Agents. 1: α–Heteroatom Substituted β–Phenylpropanoic Acids," *Bioorg. Med. Chem. Lett.*, 1996, 6(17), 2121–2126.

Keenan, R.M. et al., "Discovery of Potent Nonpeptide Vitronectin Receptor (av$β_3$) Antagonists," *J. Med. Chem.*, 1997, 40(15), 2289–2292.

McDowell, R.S. et al., "From Peptide to Non–Peptide. 2. The de Novo Design of Potent, Non–Peptidal Inhibitors of Platelet Aggregation Based on a Benzodiazepinedione Scaffold," *J. Am. Chem. Soc.*, 1994, 116, 5077–5083.

Miller, W.H. et al., "Structure–Activity Relationships in 3–Oxo–1,4–Benzodiazepine–2–Acetic Acid GPIIb/IIIa Antagonists. The 2–Benzazepine Series," *Bioorg. Med. Chem. Lett.*, 1996, 6(21), 2481–2486.

Ukai, Y. et al., "A novel synthetic inhibitor of endopeptidase–24.15," *Chemical Abstracts*, 1997, 127(2), 1 page.

Venturella, V.S. et al., "Substituted 1,3–Dihydro–4H–furo [3,4–d]–1,3–benzodiazepine–3–ones: Synthesis and Scope of the Method," *J. Heterocyclic Chem.*, 1969, 6(5), 671–679.

Wojciechowska, H. et al., "Preparation of 2,4–dinitrophenyl derivatives of tyrosine," *Chemical Abstracts*, 1968, 68(25), Abstract No. 11492r, 1 page.

Sengupta S et al. Tetradedron Lett. 36(25), 4475–8, 1995.*

Bach et al., "Anomalous optical rotation and circular dichroism of N–thioacylated.alpha.–amino acids and deriva," *Acta Chem. Scand.*, 1966, 20(10), 2781–2794.

Barrett, G.C., "Circular dichroism of N–thiobenzoyl–1–α–amino acids. III. Their circular dichroism through the near–ultraviolet wavelength range," *J. Chem. Soc.*, 1967, Section C, 1–5.

*Chemical Abstracts*, "N–[4–Thiazolidinyl)carbonyl]amino acid derivatives," 1981, 95(19), Abstract No. 169173f, 1 page.

Cornforth, J.W., "Oxazoles and Oxazolones," *Chem. Penicillin*, Princeton Book Review, 1949, pp. 688, 799, and 800.

Fu, H. et al., "Preliminary study on synthesis and antitumor activity in vitro of derivatives of timonacic," *Chemical Abstracts*, 1988, 108(17), Abstract No. 150358k, 1 page.

Harris, R.L.N. et al., *Aust. J. Chem.*, "Potential wool growth inhibitors. 2(1H)–Pyridone analogs of mimosine," 1977, 30(3), 649–655.

Hartke, K. et al., "Dithio and Thionoesters. Part 61. Synthesis of α–amino dithioesters and endothiodepeptides," *J. Prakt. Chem.*, 1996, 338(3), 251–256.

Jaynes, B.H. et al., "Synthesis and In Vivo Antibacterial Activity of Hygromycin a Analogs Modified at the $C_4$'Aryl Position," *Bioorg. Med. Chem. Letts.*, 1993, 3(8), 1531–1536.

Jepson, J.B. et al., "Reactions of α–Thioacylamino–acids. Their conversion into Thiazolones and Derivatives Thereof," *J. Chem. Soc.*, 1955, 1791–1797.

Masahiko, N., Japanese Patent No. 57–080370 published May 19, 1982, "Alpha–Methylcinnamic Acid Derivative, its Preparation and Antilipemic Agent Containing The Same," *Patent Abstracts of Japan*, 1982, 1 page.

Noike, Y., "Synthesis of Quinolizine Derivatives. VI. Synthesis of 3-Aminoquinolizines. (1). Synthesis of dl-3-Amino-, dl-3-epi-Amino-, and dl-3-epi-Dimethylaminoquinolizidines," *Yakugaku Zasshi*, 1959, 79(12), 1514–1518 (English summary included).

Ohki, S. et al., "Synthesis of quinolizine derivatives. V. Studies on Diastereoisomer of Ethyl 3-Quinolizidinecarboxylate," *Chem. Pharm. Bull.*, 1959, 7(6), 708–712.

Schultz, Von O.-E. et al., "Analogos of nuleic acid based as antimetabolites," *Arzneimittel Forschung. Drug Res.*, 1967, 17(8), 1060–1064 (English summary included).

Tsunematsu, H. et al., "Hydrolysis of phenylthiazolones of p-guanidinophenylalanine and arginine by trypsin and related enzymes," *J. Biochem.*, 1983, 94(4), 1119–1125.

Whitlock, B.J. et al., "Structure and synthesis of lathyrine," *J. Org. Chem.*, 1965, 30, 115–118.

Abraham, W.M. et al., "$\alpha_4$-Integrins Mediate Antigen-Induced Late Bronchial Responses and Prolonged Airway Hyperresponsiveness in Sheep", *J. Clin. Invest.*, 1994, 93, 776–787.

Berlin, C. et al., "$\alpha 4\beta 7$ Integrin Mediates Lymphocyte Binding to the Mucosal Vascular Addressin MAdCAM-1" *Cell*, 1993, 74, 185–195.

Binns, R.M. et al., "The Role of E-Selectin in Lymphocyte and Polymorphonuclear Cell Recruitment into Cutaneous Delayed Hypersensitivity Reactions in Sensitized Pigs", *J. Immunol.*, 1996, 157, 4094–4099.

Briskin, M.J. et al., "Structural Requirements for Mucosal Vascular Addressin Binding to Its Lymphocyte Receptor $\alpha_4\beta_7$", *J. Immunol.*, 1996, 156, 719–726.

Cardarelli, P.M. et al., "Cyclic RGD Peptide Inhibits $\alpha 4\beta 7$ Interaction with Connecting Segment 1 and Vascular Cell Adhesion Molecule", *J. Biol. Chem.*, 1994, 269(28), 18668–18673.

Corey, E.J. et al., "A Synthetic Method for Formyl → Ethynyl Conversion (RCHO → RC≡CH or RC≡CR')", *Tetradedron Lett.*, 1972, 36, 3769–3772.

Ferguson, T.A. et al., "Two integrin-binding peptides abrogate T cell-mediated immune responses in vivo", *Proc. Natl. Acad. Sci. USA*, 1991, 88, 8072–8076.

Holzmann, B. et al., "Peyer's patch-specific lymphocyte homing receptors consist of a VLA–4–like α chain associated with either of two integrin β chains, one of which is novel", *EMBO J.*, 1989, 8(6), 1735–1741.

Humphries, M.J. et al., "Mechanisms of VCAM-1 and fibronectin binding to integrin $\alpha_4\beta_1$: implications for integrin function and rational drug design", *Ciba Foundation Symposium*, 1995, 189, 177–194.

Issekutz, T.B., "Inhibition of lymphocyte Endothelial Adhesion and In Vivo Lymphocyte Migration to Cutaneous Inflammation by TA-3, a New Monoclonal Antibody to Rat LFA-1", *J. Immunol.*, 1992, 149(10), 3394–3402.

Lei, H. et al., "Efficient Synthesis of a Phosphinate Bis-Amino Acid and Its Use in the Construction of Amphiphilic Peptides", *J. Org. Chem.*, 1994, 59, 4206–4210.

Li, Z. et al., "Effect of an anti–Mo1 MAb on ozone–induced airway inflammation and airway hyperresponsiveness in dogs", *Am. J. Physiol.*, 1992, 263(6 Pt 1), L723–726.

Marlin, S.D. et al., "LFA–1 Immunodeficiency Disease", *J. Exp. Med.*, 1986, 164, 855–867.

Nagasawa, H.T. et al., "β–Substituted Cysteines as Sequestering Agents for Ethanol–Derived Acetaldehyde in Vivo", *J. Med. Chem.*, 1987, 30, 1373–1378.

Osborne, L., "Leukocyte Adhesion to Endothelium in Inflammation", *Cell*, 1990, 62, 3–6.

Osborn, L. et al., "Direct Expression Cloning of Vascular Cell Adhesion Molecule 1, a Cytokine–Induced Endothelial Protein that Binds to Lymphocytes", *Cell*, 1989, 59, 1203–1211.

Podolsky, D.K. et al., "Attenuation of Colitis in the Cotton–top Tamarin by Anti–α4 integrin Monoclonal Antibody", *J. Clin. Invest.*, 1993, 92, 372–380.

Shroff, H.N. et al., "Small Peptide Inhibitors of $\alpha_4\beta_7$ Mediated MAdCAM–1 Adhesion to Lymphocytes", *Barge. Med. Chem. Letts.*, 1996, 6(21), 2495–2500.

Sonnenberg, A., "Integrins and Their Ligands", *Curr. Topics Microbiol. Immunol.*, 1993, 184, 7–35.

Springer, T.A., "Adhesion receptors of the immune system", *Nature*, 1990, 346, 425–434.

Springer, T.A., "Traffic Signals for Lymphocyte Recirculation and Leukocyte Emigration: The Multistep Paradigm", *Cell*, 1994, 76, 301–314.

Vanderslice, P. et al., "A Cyclic Hexapeptide is a Potent Antagonist of α4 Integrins", *J. Immunol.*, 1997, 158, 1710–1718.

Yang, X., "A predominant role of integrin α4 in the spontaneous development of autoimmune diabetes in nonobese diabetic mice", *Proc. Natl. Acad. Sci. USA*, 1994, 91, 12604–12608.

Yednock, T.A., "Prevention of experimental autoimmune encephalomyelitis by antibodies against α4β1 integrin", *Nature*, 1992, 356, 63–66.

WPI/Derwent No. XP–002076854, Japanese Patent No. JP 04 193 895 A (Ajinomoto, K.K.), Jul. 13, 1992, DW9234, 1 Page, Abstract Only.

WPI/Derwent No. XP–002076855, Japanese Patent No. JP 56 049 373 A (Dainippon Pharm Co Ltd), May 2, 1981, DW8125, 1 Page, Abstract Only.

Yanagisawa, H. et al., WO 97/37970, "Preparation of phenylalkylcarboxylic acid derivatives lowering blood sugar level," *Chemical Abstracts*, 1997, Abstract 127:307307, 4 pages.

\* cited by examiner

PHENYLALANINE DERIVATIVES

This invention relates to a series of phenylalanine derivatives, to compositions containing them, to processes for their preparation, and to their use in medicine.

Over the last few years it has become increasingly clear that the physical interaction of inflammatory leukocytes with each other and other cells of the body plays an important role in regulating immune and inflammatory responses [Springer, T A. Nature, 346, 425, (1990); Springer, T. A. Cell 76, 301, (1994)]. Many of these interactions are mediated by specific cell surface molecules collectively referred to as cell adhesion molecules.

The adhesion molecules have been sub-divided into different groups on the basis of their structure. One family of adhesion molecules which is believed to play a particularly important role in regulating immune and inflammatory responses is the integrin family. This family of cell surface glycoproteins has a typical non-covalently linked heterodimer structure. At least 14 different integrin alpha chains and 8 different integrin beta chains have been identified [Sonnenberg, A. Current Topics in Microbiology and Immunology, 184, 7, (1993)]. The members of the family are typically named according to their heterodimer composition although trivial nomenclature is widespread in this field. Thus the integrin termed $\alpha 4\beta 1$ consists of the integrin alpha 4 chain associated with the integrin beta 1 chain, but is also widely referred to as Very Late Antigen 4 or VLA4. Not all of the potential pairings of integrin alpha and beta chains have yet been observed in nature and the integrin family has been subdivided into a number of subgroups based on the pairings that have been recognised [Sonnenberg, A. ibid].

The importance of cell adhesion molecules in human leukocyte function has been further highlighted by a genetic deficiency disease called Leukocyte Adhesion Deficiency (LAD) in which one of the families of leukocyte integrins is not expressed [Marlin, S. D. et al J. Exp. Med. 164, 855 (1986)]. Patients with this disease have a reduced ability to recruit leukocytes to inflammatory sites and suffer recurrent infections which in extreme cases may be fatal.

The potential to modify adhesion molecule function in such a way as to beneficially modulate immune and inflammatory responses has been extensively investigated in animal models using specific monoclonal antibodies that block various functions of these molecules [e.g. Issekutz, T. B. J. Immunol. 3394, (1992); Li, Z. et al Am. J. Physiol. 263, L723, (1992); Binns, R. M. et al J. Immunol. 157, 4094, (1996)]. A number of monoclonal antibodies which block adhesion molecule function are currently being investigated for their therapeutic potential in human disease.

One particular integrin subgroup of interest involves the $\alpha 4$ chain which can pair with two different beta chains $\beta 1$ and $\beta 7$ [Sonnenberg, A. ibid]. The $\alpha 4 \beta 1$ pairing occurs on many circulating leukocytes (for example lymphocytes, monocytes and eosinophils) although it is absent or only present at low levels on circulating neutrophils. $\alpha 4\beta 1$ binds to an adhesion molecule (Vascular Cell Adhesion Molecule-1 also known as VCAM-1) frequently up-regulated on endothelial cells at sites of inflammation [Osborne, L. Cell, 62, 3, (1990)]. The molecule has also been shown to bind to at least three sites in the matrix molecule fibronectin [Humphries, M. J. et al. Ciba Foundation Symposium, 189, 177, (1995)]. Based on data obtained with monoclonal antibodies in animal models it is believed that the interaction between $\alpha 4\beta 1$ and ligands on other cells and the extracellular matrix plays an important role in leukocyte migration and activation [Yednock, T. A. et al, Nature, 356, 63, (1992); Podolsky, D. K. et al. J. Clin. Invest. 92, 373, (1993); Abraham, W. M. et al. J. Clin. Invest. 93, 776, (1994)].

The integrin generated by the pairing of $\alpha 4$ and $\beta 7$ has been termed LPAM-1 [Holzmann, B and Weissman, I. EMBO J. 8, 1735, (1989)] and like $\alpha 4\beta 1$, binds to VCAM-1 and fibronectin. In addition, $\alpha 4\beta 7$ binds to an adhesion molecule believed to be involved in the homing of leukocytes to mucosal tissue termed MAdCAM-1 [Berlin, C. et al, Cell, 74, 185, (1993)]. The interaction between $\alpha 4\beta 7$ and MAdCAM-1 may also be important at sites of inflammation outside of mucosal tissue [Yang, X-D. et al, PNAS, 91, 12604 (1994)].

Regions of the peptide sequence recognised by $\alpha 4\beta 1$ and $\alpha 4\beta 7$ when they bind to their ligands have been identified. $\alpha 4\beta 1$ seems to recognise LDV, IDA or REDV peptide sequences in fibronectin and a QIDSP sequence in VCAM-1 [Humphries, M. J. et al, ibid] whilst $\alpha 4\beta 7$ recognises a LDT sequence in MAdCAM-1 [Briskin, M. J. et al, J. Immunol. 156, 719, (1996)]. There have been several reports of inhibitors of these interactions being designed from modifications of these short peptide sequences [Cardarelli, P. M. et al J. Biol. Chem. 269, 18668, (1994); Shroff, H. N. Bioorganic. Med. Chem. Lett. 6, 2495, (1996); Vanderslice, P. J. Immunol. 158, 1710, (1997)]. It has also been reported that a short peptide sequence derived from the $\alpha 4\beta 1$ binding site in fibronectin can inhibit a contact hypersensitivity reaction in a trinitrochlorobenzene sensitised mouse [Ferguson, T. A. et al, PNAS 88, 8072, (1991)].

Since the alpha 4 subgroup of integrins are predominantly expressed on leukocytes their inhibition can be expected to be beneficial in a number of immune or inflammatory disease states. However, because of the ubiquitous distribution and wide range of functions performed by other members of the integrin family it is very important to be able to identify selective inhibitors of the alpha 4 subgroup.

We have now found a group of compounds which are potent and selective inhibitors of $\alpha 4$ integrins. Members of the group are able to inhibit $\alpha 4$ integrins such as $\alpha 4\beta 1$ and/or $\alpha 4\beta 7$ at concentrations at which they generally have no or minimal inhibitory action on $\alpha$ integrins of other subgroups. The compounds are thus of use in medicine, for example in the prophylaxis and treatment of immune or inflammatory disorders as described hereinafter.

Thus according to one aspect of the invention we provide a compound of formula (1)

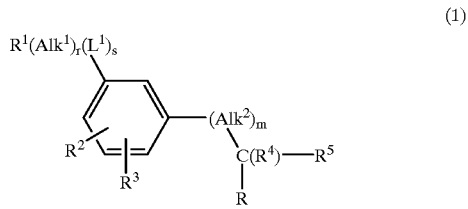

wherein
  $R^1$ is a hydrogen atom or an optionally substituted cycloaliphatic, polycycloaliphatic, heterocycloaliphatic, polyheterocycloaliphatic, aromatic or heteroaromatic group;
  $Alk^1$ is an optionally substituted aliphatic or heteroaliphatic chain;
  $L^1$ is a linker atom or group;
  r and s is each zero or an integer 1;
  $R^2$ and $R^3$, which may be the same or different, is each a hydrogen or halogen atom or a straight or branched alkyl, haloalkyl, alkoxy, haloalkoxy, hydroxyl or nitro group;

Alk$^2$ is a straight or branched alkylene chain;

m is zero or an integer 1;

R$^4$ is a hydrogen atom or a methyl group;

R$^5$ is a group —L$^2$(CH$_2$)$_t$R$^6$ in which L$^2$ is a —N(R$^7$)CO— [where R$^7$ is a hydrogen atom or a straight or branched alkyl group] or —N(R$^7$)CS— group, t is zero or the integer 1, and R$^6$ is an optionally substituted aliphatic, heteroaliphatic, cycloaliphatic, polycycloaliphatic, heterocycloaliphatic, polyheterocycloaliphatic, aromatic or heteroaromatic group; R is a carboxylic acid (—CO$_2$H) or a derivative thereof, and the salts, solvates and hydrates thereof.

It will be appreciated that compounds of formula (1) may have one or more chiral centres. Where one or more chiral centres is present, enantiomers or diastereomers may exist, and the invention is to be understood to extend to all such enantiomers, diasteromers and mixtures thereof, including racemates. Formula (1) and the formulae hereinafter are intended to represent all individual isomers and mixtures thereof, unless stated or shown otherwise.

In the compounds of formula (1), derivatives of the carboxylic acid group R include carboxylic acid esters and amides. Particular esters and amides include those —CO$_2$Alk$^5$, —CONH$_2$, —CONHR$^{12}$ and —CON[R$^{12}$]$_2$ groups described below in relation to the group R$^6$.

Alk$^2$ in the compounds of the invention may be for example a straight or branched C$_{1-3}$alkylene chain. Particular examples include —CH$_2$—, —CH(CH$_3$)— and —(CH$_2$)$_2$—.

When in the compounds of the invention L$^1$ is present as a linker atom or group it may be any divalent linking atom or group. Particular examples include —O— or —S— atoms or —C(O)—, —C(O)O—, —C(S)—, —S(O)—, —S(O)$_2$—, —N(R$^8$)— [where R$^8$ is a hydrogen atom or an optionally substituted straight or branched alkyl group], —CON(R$^8$)—, —OC(O)N(R$^8$)—, —CSN(R$^8$)—, —N(R$^8$)CO—, —N(R$^8$)C(O)O—, —N(R$^8$)CS—, —S(O)$_2$N(R$^8$)—, —N(R$^8$)S(O)$_2$—, —N(R$^8$)CSN(R$^8$)—, or —N(R$^8$)SO$_2$N(R$^8$)— groups. Where the linker group contains two R$^8$ substituents, these may be the same or different.

When Alk$^1$ and/or R$^6$ in compounds of formula (1) is an optionally substituted aliphatic chain it may be an optionally substituted C$_{1-10}$ aliphatic chain. Particular examples include optionally substituted straight or branched chain C$_{1-6}$ alkyl, C$_{2-6}$ alkenyl, or C$_{2-6}$ alkynyl chains.

Heteroaliphatic chains represented by Alk$^1$ and/or R$^6$ include the aliphatic chains just described but with each chain additionally containing one, two, three or four heteroatoms or heteroatom-containing groups. Particular heteroatoms or groups include atoms or groups L$^3$ where L$^3$ is as defined above for L$^1$ when L$^1$ is a linker atom or group. Each L$^3$ atom or group may interrupt the aliphatic chain, or may be positioned at its terminal carbon atom to connect the chain to an adjoining atom or group.

Particular examples of aliphatic chains represented by Alk$^1$ and R$^6$ include optionally substituted —CH$_2$—, —CH$_2$CH$_2$—, —CH(CH$_3$)—, —C(CH$_3$)$_2$—, —(CH$_2$)$_2$CH$_2$—, —CH(CH$_3$)CH$_2$—, —(CH$_2$)$_3$CH$_2$—, —CH(CH$_3$)CH$_2$CH$_2$—, —CH$_2$CH(CH$_3$)CH$_2$—, —C(CH$_3$)$_2$CH$_2$—, —(CH$_2$)$_4$CH$_2$—, —(CH$_2$)$_5$CH$_2$—, —CHCH—, —CHCHCH$_2$—, —CH$_2$CHCH—, —CHCHCH$_2$CH$_2$—, —CH$_2$CHCHCH$_2$—, —(CH$_2$)$_2$CHCH—, —CC—, —CCCH$_2$—, —CH$_2$CC—, —CCCH$_2$CH$_2$—, —CH$_2$CCCH$_2$—, or —(CH$_2$)$_2$CC— chains. Where appropriate each of said chains may be optionally interrupted by one or two atoms and/or groups L$^3$ to form an optionally substituted heteroaliphatic chain. Particular examples include optionally substituted —L$^3$CH$_2$—, —CH$_2$L$^3$CH$_2$—, —L$^3$(CH$_2$)$_2$—, —CH$_2$L$^3$(CH$_2$)$_2$—, —(CH$_2$)$_2$L$^3$CH$_2$—, —L$^3$(CH$_2$)$_3$— and —(CH$_2$)$_2$L$^3$(CH$_2$)$_2$— chains.

The optional substituents which may be present on aliphatic or heteroaliphatic chains represented by Alk$^1$ and R$^6$ include one, two, three or more substituents where each substituent may be the same or different and is selected from halogen atoms, e.g. fluorine, chlorine, bromine or iodine atoms, or C$_{1-6}$alkoxy, e.g. methoxy or ethoxy, thiol, C$_{1-6}$alkylthio e.g. methylthio or ethylthio, amino or substituted amino groups. Substituted amino groups include —NHR$^9$ and —N(R$^9$)$_2$ groups where R$^9$ is a straight or branched alkyl group. Where two R$^9$ groups are present these may be the same or different. Particular examples of substituted chains represented by Alk$^1$ include those specific chains just described substituted by one, two, or three halogen atoms such as fluorine atoms, for example chains of the type —CH(CF$_3$)—, —C(CF$_3$)$_2$— —CH$_2$CH(CF$_3$)—, —CH$_2$C(CF$_3$)$_2$—, —CH(CF$_3$)— and —C(CF$_3$)$_2$CH$_2$.

Optionally substituted cycloaliphatic groups represented by R$^1$ and/or R$^6$ in compounds of the invention include optionally substituted C$_{3-10}$ cycloaliphatic groups. Particular examples include optionally substituted C$_{3-10}$ cycloalkyl, e.g. C$_{3-7}$ cycloalkyl or C$_{3-10}$ cycloalkenyl, e.g. C$_{3-7}$ cycloalkenylgroups.

Optionally substituted heterocycloaliphatic groups represented by R$^1$ and/or R$^6$ include optionally substituted C$_{3-10}$heterocycloaliphatic groups. Particular examples include optionally substituted C$_{3-10}$heterocycloalkyl, e.g. C$_{3-7}$ heterocycloalkyl, or C$_{3-10}$heterocycloalkenyl, e.g. C$_{3-7}$ heterocycloalkenyl groups, each of said groups containing one, two, three or four heteroatoms or heteroatom-containing groups L$^3$ as just defined.

Optionally substituted polycycloaliphatic groups represented by R$^1$ and/or R$^6$ include optionally substitued C$_{7-10}$ bi- or tricycloalkyl or C$_{7-10}$bi- or tricycloalkenyl groups. Optionally substituted polyheterocycloaliphatic groups represented by R$^1$ and/or R$^6$ include the optionally substituted polycycloalkyl groups just described, but with each group additionally containing one, two, three or four L$^3$ atoms or groups.

Particular examples of R$^1$ and R$^7$ cycloaliphatic, polycycloaliphatic, heterocycloaliphatic and polyheterocycloaliphatic groups include optionally substituted cyclopropyl, cyclobutyl, cyclopentyl, cyclohexyl, cycloheptyl, 2-cyclobuten-1-yl, 2-cyclopenten-1-yl, 3-cyclopenten-1-yl, adamantyl, norbornyl, norbornenyl, tetrahydrofuranyl, pyrroline, e.g. 2- or 3-pyrrolinyl, pyrrolidinyl, pyrrolidinone, oxazolidinyl, oxazolidinone, dioxolanyl, e.g. 1,3-dioxolanyl, imidazolinyl, e.g. 2-imidazolinyl, imidazolidinyl, pyrazolinyl, e.g. 2-pyrazolinyl, pyrazolidinyl, pyranyl, e.g. 2- or 4-pyranyl, piperidinyl, piperidinone, 1,4-dioxanyl, morpholinyl, morpholinone, 1,4-dithianyl, thiomorpholinyl, piperazinyl, 1,3,5-trithianyl, oxazinyl, e.g. 2H-1,3-, 6H-1,3-, 6H-1,2-, 2H-1,2- or 4H-1,4-oxazinyl, 1,2,5-oxathiazinyl, isoxazinyl, e.g. o- or p-isoxazinyl, oxathiazinyl, e.g. 1,2,5 or 1,2,6-oxathiazinyl, or 1,3,5,-oxadiazinyl groups.

The optional substituents which may be present on the R$^1$ and R$^6$ cycloaliphatic, polycycloaliphatic, heterocycloaliphatic or polyheterocycloaliphatic groups include one, two, three or more substituents selected from halogen atoms, e.g. fluorine, chlorine, bromine or iodine atoms, or hydroxyl, C$_{1-6}$alkoxy, e.g. methoxy or ethoxy, thiol, C$_{1-6}$alkylthio e.g. methylthio or ethylthio, amino or substituted amino groups. Substituted amino groups include —NHR$^9$ and —N(R$^9$)$_2$ groups where R$^9$ is as defined above. Additionally, when R$^6$ is a heterocycloaliphatic group containing one or more nitrogen atoms each nitrogen atom may be optionally substituted by a group —$(L^4)_p(Alk^3)_qR^{10}$ in which $L^4$ is —C(O)—, —C(O)O—, —C(S)—, —S(O)$_2$—, —CON($R^8$)—, —CSN($R^8$)—, —SON($R^8$)— or SO$_2$N($R^8$)—; p is zero or an integer 1; $Alk^3$ is an optionally substituted aliphatic or heteroaliphatic chain; q is zero or an integer 1; and $R^{10}$ is a hydrogen atom or an optionally substituted cycloaliphatic, heterocycloaliphatic, polycycloaliphatic, polyheterocycloaliphatic, aromatic or heteroaromatic group.

Optionally substituted aliphatic or heteroaliphatic chains represented by $Alk^3$ include those optionally substituted chains described above for $Alk^1$.

Cycloaliphatic, heterocycloaliphatic, polycyloaliphatic or polyheterocycloaliphatic groups represented by $R^{10}$ include those groups just described for $R^1$ and $R^6$. Optional substituents which may be present on these groups include those described above in relation to $Alk^1$ aliphatic and heteroaliphatic chains.

Optionally substituted aromatic or heteroaromatic groups represented by $R^{10}$ include those aromatic and heteroaromatic groups generally and specifically described below for $R^1$ and/or $R^6$.

In the compounds of formula (1), optionally substituted aromatic groups represented by the groups $R^1$, $R^6$ and/or $R^{10}$ include for example optionally substituted monocyclic or bicyclic fused ring $C_{6-12}$ aromatic groups, such as optionally substituted phenyl, 1- or 2-naphthyl, 1- or 2-tetrahydronaphthyl, indanyl or indenyl groups.

Optionally substituted heteroaromatic groups, represented by the groups $R^1$, $R^6$ and/or $R^{10}$ in compounds of formula (1) include for example optionally substituted $C_{1-9}$ heteroaromatic groups containing for example one, two, three or four heteroatoms selected from oxygen, sulphur or nitrogen atoms. In general, the heteroaromatic groups may be for example monocyclic or bicyclic fused ring heteroaromatic groups. Monocyclic heteroaromatic groups include for example five- or six-membered heteroaromatic groups containing one, two, three or four heteroatoms selected from oxygen, sulphur or nitrogen atoms. Bicyclic heteroaromatic groups include for example nine- to thirteen-membered fused-ring heteroaromatic groups containing one, two or more heteroatoms selected from oxygen, sulphur or nitrogen atoms.

Particular examples of heteroaromatic groups of these types include optionally substituted pyrrolyl, furyl, thienyl, imidazolyl, N-methylimidazolyl, N-ethylimidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-thiadiazole, pyridyl, pyrimidinyl, pyridazinyl, pyrazinyl, 1,3,5-triazinyl, 1,2,4-triazinyl, 1,2,3-triazinyl, benzofuryl, [2,3-dihydro]benzofuryl, isobenzofuryl, benzothienyl, benzo-triazolyl, indolyl, isoindolyl, benzimidazolyl, imidazo[1,2-a]pyridyl, benzothiazolyl, benzoxazolyl, benzopyranyl, [3,4-dihydro]benzopyranyl, quinazolinyl, naphthyridinyl, pyrido[3,4-b]pyridyl, pyrido[3,2-b]pyridyl, pyrido[4,3-b]pyridyl, quinolinyl, isoquinolinyl, tetrazolyl, 5,6,7,8-tetrahydroquinolinyl, 5,6,7,8-tetrahydroisoquinolinyl, and imidyl, e.g. succinimidyl, phthalimidyl, or naphthalimidyl such as 1,8-naphthalimidyl.

Optional substituents which may be present on the aromatic or heteroaromatic groups represented by $R^1$, $R^6$ and/or $R^{10}$ include one, two, three or more substituents, each selected from an atom or group $R^{11}$ in which $R^{11}$ is —$R^{11a}$ or —$Alk^4(R^{11a})_m$, where $R^{11a}$ is a halogen atom, or an amino (—NH$_2$), substituted amino, nitro, cyano, amidino, hydroxyl (—OH), substituted hydroxyl, formyl, carboxyl (—CO$_2$H), esterified carboxyl, thiol (—SH), substituted thiol, —COR$^{12}$ [where $R^{12}$ is an —$Alk^4(R^{11a})_m$, aryl or heteroaryl group], —CSR$^{12}$, —SO$_3$H, —SO$_2$R$^{12}$, —SO$_2$NH$_2$, —SO$_2$NHR$^{12}$ SO$_2$N(R$^{12}$)$_2$, —CONH$_2$, —CSNH$_2$, —CONHR$^{12}$, —CSNHR$^{12}$, —CON[R$^{12}$]$_2$, —CSN(R$^{12}$)$_2$, —N(R$^8$)SO$_2$R$^{12}$, —N(SO$_2$R$^{12}$)$_2$, —N(R$^8$)SO$_2$NH$_2$, —N(R$^8$)SO$_2$NHR$^{12}$, —N(R$^8$)SO$_2$N(R$^{12}$)$_2$, —N(R$^8$)COR$^{12}$, —N(R$^8$)CON(R$^{12}$)$_2$, —N(R$^8$)CSN(R$^{12}$)$_2$, —N(R$^8$)CSR$^{12}$, —N(R$^8$)C(O)OR$^{12}$, —SO$_2$NHet$^1$ [where —NHet$^1$ is an optionally substituted $C_{5-7}$cyclicamino group optionally containing one or more other —O— or —S— atoms or —N(R$^8$)—, —C(O)— or —C(S)— groups], —CONHet$^1$, —CSNHet$^1$, —N(R$^8$)SO$_2$NHet$^1$, —N(R$^8$)CONHet$^1$, —N(R$^8$)CSNHet$^1$, —SO$_2$N(R$^8$)Het$^2$ [where Het$^2$ is an optionally substituted monocyclic $C_{5-7}$carbocyclic group optionally containing one or more —O— or —S— atoms or —N(R$^8$)—, —C(O)— or —C(S)— groups], —CON(R$^8$)Het$^2$, —CSN(R$^8$)Het$^2$, —N(R$^8$)CON(R$^8$)Het$^2$, —N(R$^8$)CSN(R$^8$)Het$^2$, aryl or heteroaryl group; $Alk^4$ is a straight or branched $C_{1-6}$alkylene, $C_{2-6}$alkenylene or $C_{2-6}$alkynylene chain, optionally interrupted by one, two or three —O— or —S— atoms or —S(O)$_n$ [where n is an integer 1 or 2] or —N(R$^{13}$)— groups [where $R^{13}$ is a hydrogen atom or $C_{1-6}$alkyl, e.g. methyl or ethyl group]; and m is zero or an integer 1, 2 or 3. It will be appreciated that when two $R^8$ or $R^{12}$ groups are present in one of the above substituents, the $R^8$ or $R^{12}$ groups may be the same or different.

When in the group —$Alk^4(R^{11a})_m$ m is an integer 1, 2 or 3, it is to be understood that the substituent or substituents $R^{11a}$ may be present on any suitable carbon atom in —$Alk^4$. Where more than one $R^{11a}$ substituent is present these may be the same or different and may be present on the same or different atom in —$Alk^4$. Clearly, when m is zero and no substituent $R^{11a}$ is present the alkylene, alkenylene or alkynylene chain represented by $Alk^4$ becomes an alkyl, alkenyl or alkynyl group.

When $R^{11a}$ is a substituted amino group it may be for example a group —NHR$^{12}$ [where $R^{12}$ is as defined above] or a group —N(R$^{12}$)$_2$ wherein each $R^{12}$ group is the same or different.

When $R^{11a}$ is a halogen atom it may be for example a fluorine, chlorine, bromine, or iodine atom.

When $R^{11a}$ is a substituted hydroxyl or substituted thiol group it may be for example a group —OR$^{12}$ or a —SR$^{12}$ or —SC(=NH)NH$_2$ group respectively.

Esterified carboxyl groups represented by the group $R^{11a}$ include groups of formula —CO$_2$Alk$^5$ wherein $Alk^5$ is a straight or branched, optionally substituted $C_{1-8}$alkyl group such as a methyl, ethyl, n-propyl, i-propyl, n-butyl, i-butyl, s-butyl or t-butyl group; a $C_{6-12}$aryl$C_{1-8}$alkyl group such as an optionally substituted benzyl, phenylethyl, phenylpropyl, 1-naphthylmethyl or 2-naphthylmethyl group; a $C_{6-12}$aryl group such as an optionally substituted phenyl, 1-naphthyl or 2-naphthyl group; a $C_{6-12}$aryloxy$C_{1-8}$alkyl group such as an optionally substituted phenyloxymethyl, phenyloxyethyl, 1-naphthyl-oxymethyl, or 2-naphthyloxymethyl group; an optionally substituted $C_{1-8}$alkanoyloxy$C_{1-8}$alkyl group, such as a pivaloyloxymethyl, propionyloxyethyl or propionyloxypropyl group; or a $C_{6-12}$aroyloxy$C_{1-8}$alkyl group such as an optionally substituted benzoyloxyethyl or benzoyloxypropyl group. Optional substituents present on the $Alk^5$ group include $R^{11a}$ substituents described above.

When $Alk^4$ is present in or as a substituent it may be for example a methylene, ethylene, n-propylene, i-propylene, n-butylene, i-butylene, s-butylene, t-butylene, ethenylene, 2-propenylene, 2-butenylene, 3-butenylene, ethynylene, 2-propynylene, 2-butynylene or 3-butynylene chain, optionally interrupted by one, two, or three —O— or —S—, atoms or —S(O)—, —S(O)$_2$— or —N(R$^8$)— groups.

Aryl or heteroaryl groups represented by the groups R$^{11a}$ or R$^{12}$ include mono- or bicyclic optionally substituted C$_{6-12}$ aromatic or C$_{1-9}$ heteroaromatic groups as described above for the group R$^6$. The aromatic and heteroaromatic groups may be attached to the remainder of the compound of formula (1) by any carbon or hetero e.g. nitrogen atom as appropriate.

When —NHet$^1$ or —Het$^2$ forms part of a substituent R$^{11}$ each may be for example an optionally substituted pyrrolidinyl, pyrazolidinyl, piperazinyl, morpholinyl, thiomorpholinyl, piperidinyl or thiazolidinyl group. Additionally Het$^2$ may represent for example, an optionally substituted cyclopentyl or cyclohexyl group. Optional substituents which may be present on —NHet$^1$ or —Het$^2$ include those substituents described above in relation to Alk$^1$ chains.

Particularly useful atoms or groups represented by R$^{11}$ include fluorine, chlorine, bromine or iodine atoms, or C$_{1-6}$alkyl, e.g. methyl, ethyl, n-propyl, i-propyl, n-butyl or t-butyl, optionally substituted phenyl, pyridyl, pyrrolyl, furyl, thiazolyl, or thienyl, C$_{1-6}$alkylamino, e.g. methylamino or ethylamino, C$_{1-6}$hydroxyalkyl, e.g. hydroxymethyl or hydroxyethyl, carboxyC$_{1-6}$alkyl, e.g. carboxyethyl, C$_{1-6}$alkylthio e.g. methylthio or ethylthio, carboxyC$_{1-6}$alkylthio, e.g. carboxymethylthio, 2-carboxyethylthio or 3-carboxy-propylthio, C$_{1-6}$alkoxy, e.g. methoxy or ethoxy, hydroxyC$_{1-6}$alkoxy, e.g. 2-hydroxyethoxy, optionally substituted phenoxy, pyridyloxy, thiazolyoxy, phenylthio or pyridylthio, C$_{5-7}$cycloalkoxy, e.g. cyclopentyloxy, haloC$_{1-6}$alkyl, e.g. trifluoromethyl, haloC$_{1-6}$alkoxy, e.g. trifluoromethoxy, C$_{1-6}$alkylamino, e.g. methylamino or ethylamino, amino (—NH$_2$), aminoC$_{1-6}$alkyl, e.g. aminomethyl or aminoethyl, C$_{1-6}$dialkylamino, e.g. dimethylamino or diethylamino, C$_{1-6}$alkylaminoC$_{1-6}$alkyl, e.g. ethylaminoethyl, C$_{1-6}$dialkylaminoC$_{1-6}$alkyl, e.g. diethylaminoethyl, aminoC$_{1-6}$alkoxy, e.g. aminoethoxy, C$_{1-6}$alkylaminoC$_6$alkoxy, e.g. methylaminoethoxy, C$_{1-6}$dialkylaminoC$_{1-6}$alkoxy, e.g. dimethylaminoethoxy, diethylaminoethoxy, isopropylaminoethoxy, or dimethylaminopropoxy, imido, such as phthalimido or naphthalimido, e.g. 1,8-naphthalimido, nitro, cyano, amidino, hydroxyl (—OH), formyl [HC(O)—], carboxyl (—CO$_2$H), —CO$_2$Alk$^6$ [where Alk$^6$ is as defined above], C$_{1-6}$ alkanoyl e.g. acetyl, optionally substituted benzoyl, thiol (—SH), thioC$_{1-6}$alkyl, e.g. thiomethyl or thioethyl, —SC(=NH)NH$_2$, sulphonyl (—SO$_3$H), C$_{1-6}$alkylsulphonyl, e.g. methyl-sulphonyl, aminosulphonyl (—SO$_2$NH$_2$), C$_{1-6}$alkylaminosulphonyl, e.g. methylaminosulphonyl or ethylaminosulphonyl, C$_{1-6}$dialkylaminosulphonyl, e.g. dimethylaminosulphonyl or diethylaminosulphonyl, phenylamino-sulphonyl, carboxamido (—CONH$_2$), C$_{1-6}$alkylaminocarbonyl, e.g. methylaminocarbonyl or ethylaminocarbonyl, C$_{1-6}$dialkylaminocarbonyl, e.g. dimethylaminocarbonyl or diethylaminocarbonyl, aminoC$_{1-6}$alkylaminocarbonyl, e.g. aminoethylaminocarbonyl, C$_{1-6}$dialkylamino C$_{1-6}$alkylaminocarbonyl, e.g. diethylaminoethylaminocarbonyl, aminocarbonylamino, C$_{1-6}$alkylaminocarbonylamino, e.g. methylaminocarbonylamino or ethylaminocarbonylamino, C$_{1-6}$dialkylaminocarbonylamino, e.g. dimethylaminocarbonylamino or diethylaminocarbonylamino, C$_{1-6}$alkylaminocabonylC$_{1-6}$alkylamino, e.g. methylaminocarbonylmethylamino, aminothiocarbonylamino, C$_{1-6}$alkylaminothiocarbonylamino, e.g. methylaminothiocarbonylamino or ethylaminothiocarbonylamino, C$_{1-6}$dialkylaminothiocarbonylamino, e.g. dimethylaminothiocarbonylamino or diethylaminothiocarbonylamino, C$_{1-6}$alkylaminothiocarbonylC$_{1-6}$alkylamino, e.g. ethylaminothiocarbonylmethylamino, —CONHC(=NH)NH$_2$, C$_{1-6}$alkylsulphonylamino, e.g. methylsulphonylamino or ethylsulphonylamino, C$_{1-6}$dialkylsulphonylamino, e.g. dimethylsulphonylamino or diethylsulphonylamino, optionally substituted phenylsulphonylamino, aminosulphonylamino (—NHSO$_2$NH$_2$), C$_{1-6}$alkylaminosulphonylamino, e.g. methylaminosulphonyl-amino or ethylaminosulphonylamino, C$_{1-6}$dialkylaminosulphonylamino, e.g. dimethylaminosulphonylamino or diethylaminosulphonylamino, optionally substituted morpholinesulphonylamino or morpholinesulphonylC$_{1-6}$alkylamino, optionally substituted phenylaminosulphonylamino, C$_{1-6}$alkanoylamino, e.g. acetylamino, aminoC$_{1-6}$alkanoylamino e.g. aminoacetylamino, C$_{1-6}$dialkylaminoC$_{1-6}$alkanoylamino, e.g. dimethylaminoacetylamino, C$_{1-6}$alkanoylaminoC$_{1-6}$alkyl, e.g. acetylaminomethyl, C$_{1-6}$alkanoylaminoC$_{1-6}$alkylamino, e.g. acetamidoethylamino, C$_{1-6}$alkoxycarbonylamino, e.g. methoxycarbonylamino, ethoxycarbonylamino or t-butoxycarbonylamino or optionally substituted benzyloxy, pyridylmethoxy, thiazolylmethoxy, benzyloxycarbonylamino, benzyloxycarbonylaminoC$_1$ 6alkyl e.g. benzyloxycarbonylaminoethyl, benzothio, pyridylmethylthio or thiazolylmethylthio groups.

Where desired, two R$^{11}$ substituents may be linked together to form a cyclic group such as a cyclic ether, e.g. a C$_{1-6}$alkylenedioxy group such as methylenedioxy or ethylenedioxy.

It will be appreciated that where two or more R$^{11}$ substituents are present, these need not necessarily be the same atoms and/or groups. In general, the substituent(s) may be present at any available ring position in the aromatic or heteroaromatic group represented by R$^1$, R$^6$ and/or R$^{11}$.

Alkyl groups represented by the groups R$^2$ or R$^3$ in compounds of the invention include for example straight or branched C$_{1-6}$alkyl groups such as methyl, ethyl, n-propyl, i-propyl, n-butyl, i-butyl, s-butyl or t-butyl groups. Alkoxy groups represented by the groups R$^2$ or R$^3$ include straight or branched C16alkoxy groups such as methoxy or ethoxy groups. Halogen atoms represented by the groups R$^2$ or R$^3$ include for example fluorine, chlorine, bromine or iodine atoms. When R$^2$ and/or R$^3$ is a haloalkyl or haloalkoxy group it may be for example a haloC$_{1-6}$alkyl or haloC$_{1-6}$alkoxy group containing one, two or three halogen atoms selected from fluorine, chlorine, bromine or iodine atoms. Particular examples of groups of this type include —CF$_3$, —OCF$_3$, —CCl$_3$, —OCCl$_3$, —CHF$_2$, —OCHF$_2$, —CHCl$_2$, —OCHCl$_2$, —CH$_2$F, —OCH$_2$F, —CH$_2$Cl and —OCH$_2$Cl groups.

Straight or branched alkyl groups represented by R$^7$, R$^8$ and/or R$^9$ in compounds of the invention include straight or branched C$_{1-6}$alkyl e.g. C$_{1-3}$alkyl groups such as methyl or ethyl groups. Each R$^8$ group may be optionally substituted, for example by one or more atoms or groups of the types described previously as optional Alk$^1$ substituents.

The presence of certain substituents in the compounds of formula (1) may enable salts of the compounds to be formed. Suitable salts include pharmaceutically acceptable salts, for example acid addition salts derived from inorganic or organic acids, and salts derived from inorganic and organic bases.

Acid addition salts include hydrochlorides, hydrobromides, hydroiodides, alkylsulphonates, e.g. methanesulphonates, ethanesulphonates, or isethionates, arylsulphonates, e.g. p-toluenesulphonates, besylates or napsylates, phosphates, sulphates, hydrogen sulphates, acetates, trifluoroacetates, propionates, citrates, maleates, fumarates, malonates, succinates, lactates, oxalates, tartrates and benzoates.

Salts derived from inorganic or organic bases include alkali metal salts such as sodium or potassium salts, alkaline earth metal salts such as magnesium or calcium salts, and organic amine salts such as morpholine, piperidine, dimethylamine or diethylamine salts.

Particularly useful salts of compounds according to the invention include pharmaceutically acceptable salts, especially acid addition pharmaceutically acceptable salts.

Generally in the compounds of the invention the group R is preferably a —$CO_2H$ group.

$Alk^2$ in compounds of formula (1) is preferably a —$CH_2$— chain and m is preferably an integer 1.

$R^4$ in compounds of the invention is preferably a hydrogen atom.

In general in compounds of formula (1) —$(Alk^1)_r(L^1)_s$— is preferably —$CH_2O$— or —$CON(R^8)$—, particularly —CONH—.

The group $R^1$ in compounds of formula (1) is preferably an optionally substituted aromatic or heteroaromatic group. Particularly useful groups of these types include optionally substitued phenyl, pyridyl or pyrimidinyl groups. Where optional substituents are present in these groups they may in particular be selected from one or two fluorine, chlorine, bromine or iodine atoms, or $C_{1-6}$alkyl, $C_{1-6}$alkylamino, $C_{1-6}$hydroxyalkyl, carboxy$C_{1-6}$alkyl, $C_{1-6}$alkylthio, carboxy$C_{1-6}$alkylthio, $C_{1-6}$alkoxy, hydroxy$C_{1-6}$alkoxy, halo$C_{1-6}$alkyl, halo$C_{1-6}$alkoxy, $C_{1-6}$alkylamino, amino (—$NH_2$), amino$C_{1-6}$alkyl, $C_{1-6}$dialkylamino, $C_{1-6}$alkylamino$C_{1-6}$alkyl, $C_{1-6}$dialkylamino$C_{1-6}$alkyl, amino$C_{1-6}$alkoxy, $C_{1-6}$alkylamino$C_{1-6}$alkoxy, $C_{1-6}$dialkylamino$C_{1-6}$alkoxy, nitro, cyano, hydroxyl (—OH), formyl [HC(O)—], carboxyl (—$CO_2H$), —$CO_2Alk^6$, $C_{1-6}$ alkanoyl, thiol (—SH), thio$C_{1-6}$alkyl, sulphonyl (—$SO_3H$), $C_{1-6}$alkylsulphonyl, aminosulphonyl (—$SO_2NH_2$), $C_{1-6}$alkylaminosulphonyl, $C_{1-6}$dialkylaminosulphonyl, carboxamido (—$CONH_2$), $C_{1-6}$alkylaminocarbonyl, e.g. methylaminocarbonyl or ethylaminocarbonyl, $C_{1-6}$dialkylaminocarbonyl, amino$C_{1-6}$alkylaminocarbonyl, $C_{1-6}$dialkylamin-$C_{1-6}$alkylaminocarbonyl, aminocarbonylamino, $C_{1-6}$alkylaminocarbonylamino, $C_{1-6}$dialkylaminocarbonylamino, $C_{1-6}$alkylaminocabonyl$C_{1-6}$alkylamino, $C_{1-6}$alkylaminothiocarbonylamino, $C_{1-6}$dialkylaminothiocarbonylamino, $C_{1-6}$alkylaminothiocarbonyl$C_{1-6}$alkylamino, $C_{1-6}$alkylsulphonylamino, $C_{1-6}$dialkylsulphonylamino, aminosulphonylamino (—$NHSO_2NH_2$), $C_{1-6}$alkylaminosulphonylamino, $C_{1-6}$dialkylaminosulphonylamino, $C_{1-6}$ alkanoylamino, amino$C_{1-6}$alkanoylamino, $C_{1-6}$dialkylamino $C_{1-6}$alkanoylamino, $C_{1-6}$alkanoylamino$C_{1-6}$alkyl, $C_{1-6}$alkanoylamino$C_{1-6}$alkylamino, or $C_{1-6}$alkoxycarbonylamino groups, especially as more particularly defined herein.

Particularly useful classes of compounds according to the invention are those wherein $R^5$ is a —$NHCOR^6$ or —$NHCSR^6$ group.

In general, $R^6$ in the group —$L^2(CH_2)_tR^6$ may especially be an optionally substituted cycloaliphatic, heterocycloaliphatic, aromatic or heteroaromatic group as defined herein. Particularly useful groups of this type include optionally substituted $C_{5-7}$heterocycloaliphatic, especially optionally substituted pyrrolidinyl or thiazolidinyl, optionally substituted phenyl and optionally substituted $C_{5-7}$heteroaromatic, especially optionally substituted pyridyl groups. Optional substituents on these groups include in particular $R^{11}$ atoms or groups where the group is an aromatic or heteroaromatic group and —$(L^4)_p(Alk^3)_qR^{10}$ groups as described earlier where the group is a nitrogen-containing heterocycloaliphatic group such as a pyrrolidinyl or thiazolidinyl group. Particularly useful —$(L^4)_p(Alk^3)_qR^{10}$ groups include those in which $L^3$ is a —CO— group. $Alk^3$ in these groups is preferably present (i.e. q is preferably an integer 1) and in particular is a —$CH_2$-chain. Compounds of this type in which $R^{10}$ is a hydrogen atom or an optionally substituted aromatic or heteroaromatic group, especially an optionally substituted phenyl, pyridinyl or imidazolyl group are particularly preferred.

Particularly useful compounds according to the invention include:

N-Acetyl-D-thioproline-3-[(2,6-dichloroisonicotinoyl) amino]-DL-phenylalanine;

N-Acetyl-D-thioproline-3-[(4-methoxyphenylacetyl) amino]-DL-phenylalanine;

N-Acetyl-D-thioproline-3-[(2,6-dichlorophenylacetyl) amino]-DL-phenylalanine;

2-Chloronicotinoyl-(0-2,6-dichlorobenzyl)-DL-m-tyrosine;

and the salts, solvates and hydrates thereof.

Compounds according to the invention are potent and selective inhibitors of α4 integrins. The ability of the compounds to act in this way may be simply determined by employing tests such as those described in the Examples hereinafter.

The compounds are of use in modulating cell adhesion and in particular are of use in the prophylaxis and treatment of diseases or disorders involving inflammation in which the extravasation of leukocytes plays a role. The invention extends to such uses and to the use of the compounds for preparing a medicament for treating these diseases and disorders. Particular diseases or disorders of this type includeinflammatory arthritis such as rheumatoid arthritis vasculitis or polydermatomyositis, multiple sclerosis, allograft rejection, diabetes, inflammatory dermatoses such as psoriasis or dermatitis, asthma and inflammatory bowel disease.

For the prophylaxis or treatment of disease the compounds according to the invention may be administered as pharmaceutical compositions, and according to a further aspect of the invention we provide a pharmaceutical composition which comprises a compound of formula (1) together with one or more pharmaceutically acceptable carriers, excipients or diluents.

Pharmaceutical compositions according to the invention may take a form suitable for oral, buccal, parenteral, nasal, topical or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds for formula (1) may be formulated for parenteral administration by injection e.g. by bolus injection or infusion. Formulations for injection may be presented in unit dosage form, e.g. in glass ampoule or multi dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (1) may also be formulated as a depot preparation. Such long acting formulations may be administered by implantation or by intramuscular injection.

For nasal administration or administration by inhalation, the compounds for use according to the present invention are conveniently delivered in the form of an aerosol spray presentation for pressurised packs or a nebuliser, with the use of suitable propellant, e.g. dichlorodifluoromethane, trichloro-fluoromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

The quantity of a compound of the invention required for the prophylaxis or treatment of a particular condition will vary depending on the compound chosen, and the condition of the patient to be treated. In general, however, daily dosages may range from around 100 ng/kg to 100 mg/kg e.g. around 0.01 mg/kg to 40 mg/kg body weight for oral or buccal administration, from around 10 ng/kg to 50 mg/kg body weight for parenteral administration and around 0.05 mg to around 1000 mg e.g. around 0.5 mg to around 1000 mg for nasal administration or administration by inhalation or insufflation.

The compounds of the invention may be prepared by a number of processes as generally described below and more specifically in the Examples hereinafter. In the following process description, the symbols R, $R^1$–$R^5$, $L^1$, $Alk^1$, $Alk^2$, m, r and s when used in the formulae depicted are to be understood to represent those groups described above in relation to formula (1) unless otherwise indicated. In the reactions described below, it may be necessary to protect reactive functional groups, for example hydroxy, amino, thio or carboxy groups, where these are desired in the final product, to avoid their unwanted participation in the reactions. Conventional protecting groups may be used in accordance with standard practice [see, for example, Green, T. W. in "Protective Groups in Organic Synthesis", John Wiley and Sons, 1991]. In some instances, deprotection may be the final step in the synthesis of a compound of formula (1) and the processes according to the invention described hereinafter are to be understood to extend to such removal of protecting groups.

Thus according to a further aspect of the invention, a compound of formula (1) in which R is a —$CO_2H$ group may be obtained by hydrolysis of an ester of formula (2):

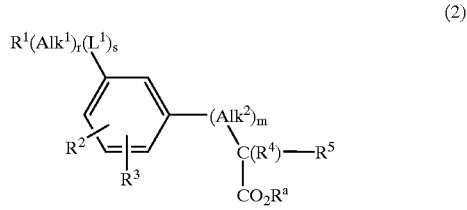

(2)

where $R^a$ is an alkyl group, for example a $C_{1-6}$alkyl group such as a methyl or ethyl group.

The hydrolysis may be performed using either an acid or a base depending on the nature of $R^a$, for example an organic acid such as trifluoroacetic acid or an inorganic base such as lithium hydroxide optionally in an aqueous organic solvent such as an amide, e.g. a substituted amide such as dimethylformamide, an ether, e.g. a cyclic ether such as tetrahydrofuran or dioxane or an alcohol, e.g. methanol at around ambient temperature. Where desired, mixtures of such solvents may be used.

Esters of formula (2) in which $R^5$ is a —$N(R^7)CO(CH_2)_tR^6$ group may be prepared by coupling an amine of formula (3):

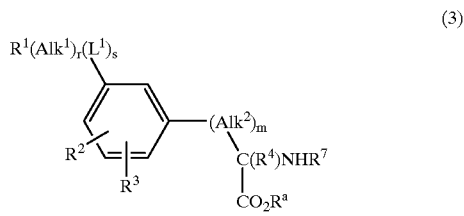

(3)

or a salt thereof with an acid $R^6(CH_2)_tCO_2H$ or an active derivative thereof. Active derivatives of acids include anhydrides, esters and halides.

The coupling reaction may be performed using standard conditions for reactions of this type. Thus for example the reaction may be carried out in a solvent, for example an inert organic solvent such as an amide, e.g. a substituted amide such as dimethylformamide, an ether, e.g. a cyclic ether such as tetrahydrofuran, or a halogenated hydrocarbon, such as dichloromethane, at a low temperature, e.g. around −30° C. to around ambient temperature, optionally in the presence of a base, e.g. an organic base such as an amine, e.g. triethylamine, pyridine, or dimethyl-aminopyridine, or a cyclic amine, such as N-methylmorpholine.

Where an acid $R^6(CH_2)_tCO_2H$ is used, the reaction may additionally be performed in the presence of a condensing agent, for example a diimide such as 1-(3-dimethylaminopropyl)-3-ethylcarbodiimide or N,N'-dicyclo-hexylcarbodiimide, advantageously in the presence of a catalyst such as a N-hydroxy compound e.g. a N-hydroxytriazole such as 1-hydroxy-benzotriazole. Alternatively, the acid may be reacted with a chloroformate, for example ethylchloroformate, prior to reaction with the amine of formula (2).

Esters of formula (2) in which $R^5$ is a —$N(R^7)CS(CH_2)_r$ $R^6$ group may be prepared by treating a corrsponding ester in which $R^5$ is a —$N(R^7)CO(CH_2)_rR^6$ group with a thiation reagent, such as Lawesson's Reagent, in an anhydrous solvent, for example a cyclic ether such as tetrahydrofuran, at an elevated temperature such as the reflux temperature.

This reaction may not be particularly suitable with starting materials in which other carbonyl groups are present, for example in $L^1$ and/or $R^6$, and which might undesirably participate in the reaction. To avoid this the reaction with the thiation reagent may be performed earlier in the synthesis of the compound of the invention with an intermediate in which other carbonyl groups are absent and any required carbonyl groups then subsequently introduced by for example acylation as generally described hereinafter.

The amines of formula (3) may be obtained from simpler, known compounds by one or more standard synthetic methods employing substitution, oxidation, reduction or cleavage reactions. Particular substitution approaches include conventional alkylation, arylation, heteroarylation, acylation, thioacylation, halogenation, sulphonylation, nitration, formylation and coupling procedures. It will be appreciated that these methods may also be used to obtain or modify other compounds of formulae (1) and (2) where appropriate functional groups exist in these compounds. Additionally, although many of the acid intermediates $R^6(CH_2)_rCO_2H$ for use in the coupling reaction described above are known, other desired acids can be derived therefrom using these standard synthetic methods.

Thus, for example compounds of formulae (1), (2) and (3) and acids $R^6(CH_2)_rCO_2H$ may be prepared by alkylation, arylation or heteroarylation. For example compounds containing a $L^1H$ or $L^4H$ group may be alkylated or arylated using a reagent $R^1(Alk^1)_rX$, or $R^{10}(Alk^3)_qX$ in which X is a leaving atom or group such as a halogen atom, e.g. a fluorine, bromine, iodine or chlorine atom or a sulphonyloxy group such as an alkylsulphonyloxy, e.g. trifluoromethyl-sulphonyloxy or arylsulphonyloxy, e.g. p-toluenesulphonyloxy group.

The alkylation or arylation reaction may be carried out in the presence of a base such as a carbonate, e.g. caesium or potassium carbonate, an alkoxide, e.g. potassium t-butoxide, or a hydride, e.g. sodium hydride, in a dipolar aprotic solvent such as an amide, e.g. a substituted amide such as dimethylformamide or an ether, e.g. a cyclic ether such as tetrahydro-furan.

In another example, compounds of formulae (1), (2) and (3) containing a $L^1H$ group (where $L^1$ is for example a —NH— group) and acids $R^6(CH_2)_rCO_2H$ may be functionalised by acylation or thioacylation, for example by reaction with a reagent $R^1(Alk^1)_rL^1X$, [wherein $L^1$ is a —C(O)—, —C(S)—, —$N(R^8)C(O)$ or —$N(R^8)C(S)$— group], $R^{10}(Alk^3)_qCOX$ or $R^{10}(Alk^3)_qNHCOX$ in the presence of a base, such as a hydride, e.g. sodium hydride or an amine, e.g. triethylamine or N-methylmorpholine, in a solvent such as a halogenated hydrocarbon, e.g. dichloromethane or carbon tetrachloride or an amide, e.g. dimethylformamide, at for example ambient temperature, or by reaction with $R^1(Alk^1)_rCO_2H$ or $R^{10}(Alk^3)_qCO_2H$ or an activated derivative thereof, for example as described above for the preparation of esters of formula (2).

In a further example a compound may be obtained by sulphonylation of a compound where $R^1(Alk^1)_r(L^1)_s$ is an —OH group by reaction with a reagent $R^1(Alk^1)_rL^1Hal$ [in which $L^1$ is —S(O)— or —$SO_2$— and Hal is a halogen atom such as a chlorine atom] in the presence of a base, for example an inorganic base such as sodium hydride in a solvent such as an amide, e.g. a substituted amide such as dimethylformamide at for example ambient temperature.

In another example, a compound where $R^1(Alk^1)_r(L^1)_s$ is a —$L^1H$ group, may be coupled with a reagent $R^1OH$ (where $R^1$ is other than a hydrogen atom) or $R^1Alk^1OH$ in a solvent such as tetrahydrofuran in the presence of a phosphine, e.g. triphenylphosphine and an activator such as diethyl, diisopropyl- or dimethylazodicarboxylate to yield a compound containing a $R^1(Alk^1)_rO$— group.

In a further example, ester groups —$CO_2Alk^5$ in the compounds may be converted to the corresponding acid [—$CO_2H$] by acid- or base-catalysed hydrolysis depending on the nature of the group $Alk^5$ using the reactants and conditions described above for the hydrolysis of esters of formula (2).

In another example, —$OR^{12}$ groups [where $R^{12}$ represents an alkyl group such as methyl group] in compounds of formulae (1) or (2) may be cleaved to the corresponding alcohol —OH by reaction with boron tribromide in a solvent such as a halogenated hydrocarbon, e.g. dichloromethane at a low temperature, e.g. around −78° C.

Alcohol [—OH] groups may also be obtained by hydrogenation of a corresponding —$OCH_2R^{12}$ group (where $R^{12}$ is an aryl group) using a metal catalyst, for example palladium on a support such as carbon in a solvent such as ethanol in the presence of ammonium formate, cyclohexadiene or hydrogen, from around ambient to the reflux temperature. In another example, —OH groups may be generated from the corresponding ester [—$CO_2Alk^5$] or aldehyde [—CHO] by reduction, using for example a complex metal hydride such as lithium aluminium hydride or sodium borohydride in a solvent such as methanol.

Aminosulphonylamino [—$NHSO_2NH_2$] groups in the compounds may be obtained, in another example, by reaction of a corresponding amine [—$NH_2$] with sulphamide in the presence of an organic base such as pyridine at an elevated temperature, e.g. the reflux temperature.

In a further example amine (—$NH_2$) groups may be alkylated using a reductive alkylation process employing an aldehyde and a borohydride, for example sodium triacetoxyborohyride or sodium cyanoborohydride, in a solvent such as a halogenated hydrocarbon, e.g. dichloromethane, a ketone such as acetone, or an alcohol, e.g. ethanol, where necessary in the presence of an acid such as acetic acid at around ambient temperature.

In a further example, amine [—$NH_2$] groups in compounds of formulae (1) or (2) may be obtained by hydrolysis from a corresponding imide by reaction with hydrazine in a solvent such as an alcohol, e.g. ethanol at ambient temperature.

In another example, a nitro [—$NO_2$] group may be reduced to an amine [—$NH_2$], for example by catalytic hydrogenation using for example hydrogen in the presence of a metal catalyst, for example palladium on a support such as carbon in a solvent such as an ether, e.g. tetrahydrofuran or an alcohol e.g. methanol, or by chemical reduction using for example a metal, e.g. tin or iron, in the presence of an acid such as hydrochloric acid.

Aromatic halogen substituents in the compounds may be subjected to halogen-metal exchange with a base, for example a lithium base such as n-butyl or t-butyl lithium, optionally at a low temperature, e.g. around −78° C., in a solvent such as tetrahydrofuran and then quenched with an electrophile to introduce a desired substituent. Thus, for example, a formyl group may be introduced by using dimethylformamide as the electrophile; a thiomethyl group may be introduced by using dimethyidisulphide as the electrophile.

In another example, sulphur atoms in the compounds, for example when present in a linker group $L^1$ or $L^3$ may be oxidised to the corresponding sulphoxide or sulphone using an oxidising agent such as a peroxy acid, e.g. 3-chloroperoxybenzoic acid, in an inert solvent such as a halogenated hydrocarbon, e.g. dichloromethane, at around ambient temperature.

N-oxides of compounds of formula (1) may be prepared for example by oxidation of the corresponding nitrogen base using an oxidising agent such as hydrogen peroxide in the presence of an acid such as acetic acid, at an elevated temperature, for example around 70° C. to 80° C., or alternatively by reaction with a peracid such as peracetic acid in a solvent, e.g. dichloromethane, at ambient temperature.

Salts of compounds of formula (1) may be prepared by reaction of a compound of formula (1) with an appropriate base in a suit able solvent or mixture of solvents e.g. an organic solvent such as an ether e.g. diethylether, or an alcohol, e.g. ethanol using conventional procedures.

Where it is desired to obtain a particular enantiomer of a compound of formula (1) this may be produced from a corresponding mixture of enantiomers using any suitable conventional procedure for resolving enantiomers.

Thus for example diastereomeric derivatives, e.g. salts, may be produced by reaction of a mixture of enantiomers of formula (1) e.g. a racemate, and an appropriate chiral compound, e.g. a chiral base. The diastereomers may then be separated by any convenient means, for example by crystallisation and the desired enantiomer recovered, e.g. by treatment with an acid in the instance where the diastereomer is a salt.

In another resolution process a racemate of formula (1) may be separated using chiral High Performance Liquid Chromatography. Alternatively, if desired a particular enantiomer may be obtained by using an appropriate chiral intermediate in one of the processes described above.

The following Examples illustrate the invention. All temperatures are in ° C. The following abbreviations are used:

| | |
|---|---|
| EDC - 1-(3-dimethylaminopropyl)3-ethycarbodiimide; | |
| DMF - dimethylformamide; | DMSO - dimethylsulphoxide; |
| HOBT - 1-hydroxybenzotriazole; | THF - tetrahydrofuran; |
| TFA - trifluoroacetic acid; | NMM - N-methylmorpholine; |
| DCM - dichloromethane; | Ph - phenyl; |
| BOC - tert-butoxycarbonyl; | EtOAc - ethyl acetate; |
| MeOH - methanol; | LDA - lithium diisopropylamide |
| tyr - tyrosine; | Ar - aryl; |
| HetAr - heteroaryl; | pyr - pyridine; |
| thiopro - thioproline; | Bu - butyl |
| Me - methyl | |

Intermediate 1

3-Nitro-DL -phenylalanine ethyl ester

LDA (2M in heptane/THF/ethyl benzene, 25.45 ml, 50.9 mmol) was added dropwise to a solution of ethyl N-(diphenylmethylene)glycinate (13 g, 48.5 mmol) in THF (200 ml) at −78°. After 40 min a solution of 3-nitrobenzyl bromide (10 g, 46.3 mmol) in THF (40 ml) was added dropwise. The mixture was stirred for 2 h and then partitioned between EtOAc (100 ml) and water (100 ml). The aqueous layer was separated and extracted with EtOAc (2×50 ml) and the combined organics dried ($Na_2SO_4$) and evaporated in vacuo. The residue was then dissolved in ethanol (200 ml) and hydrochloric acid (1M, 50 ml) was added and the mixture stirred for 0.25 h. The volatiles were then removed in vacuo and the residue purified by chromatography ($SiO_2$, $Et_2O$) to give the title compound as an orange oil (10.0 g, 96%). δH ($CDCl_3$) 8.09–8.06 (2H, m, Ar), 7.56–7.53 (1H, m, ArH), 7.48–7.43 (1H, m, ArH), 4.15 (2H, q, J 7.2, $OCH_2CH_3$), 3.71 (1H, dd, J 7.8, 5.5 Hz, $CHCH_2$), 3.14 (1H, dd, J 13.7, 5.5 Hz, $CHCH_AH_B$)2.95 (1H, dd, J 13.7, 7.8 Hz, $CHCH_AH_B$), 1.51 (2H, br s, $NH_2$) and 1.23 (3H, t, J 7.2, $OCH_2CH_3$); m/z (ESI, 60V) 239 ($M^+$+1).

Intermediate 2 a) N-Acetyl-D-thioproline-(3-nitro)-DL-phenylalanine ethyl ester

To a solution of Intermediate 1 (5.3 g, 22.3 mmol) and N-acetyl-D-thioproline (3.9 g, 22.3 mmol) in DCM (100 ml) was added NMM (2.67 ml, 24.4 mmol) HOBT (3.15 g, 23.3 mmol) and EDC (4.51 g, 23.3 mmol). The mixture was stirred at room temperature overnight. The solution was then diluted with DCM (100 ml) and washed with aqueous HCl (1M, 75 ml), saturated aqueous $NaHCO_3$ (75 ml), water (75 ml) and brine (75 ml), dried ($Na_2SO_4$) and evaporated in vacuo. The residue was purified by chromatography ($SiO_2$, DCM/MeOH, 97:3) to give the title compound as a viscous oil which solidified on standing (7.25 g, 82%). δH ($CDCl_3$) 8.10–8.08 (1H, m, ArH), 7.9–7.96 (1H, m, ArH), 7.50–7.42 (2H, m, ArH), 7.28–7.13 (1H, m, NH), 5.02–4.02 (1H, m), and 4.81–4.77 (1H, m) and 4.58–4.43 (2H, m) together (4H, 2×CHα+$NCH_2S$), 4.22–4.14 (2H, m, $OCH_2CH_3$), 3.52–3.03 (4H, m, $CH_2Ar$+$CHCH_2S$), 2.15 (s) and 2.13 (s) together (3H, $CH_3CO$) and 1.29–1.23 (3H, m, $OCH_2CH_3$); m/z (ESI; 60V) 396 ($M^+$+1).

The following compound was prepared in a similar manner:

b) N-Acetyl-L-thioproline-D,L-tyrosine methyl ester from N-acetyl-L-thioproline and methyl D,L-meta tyrosine. The crude product was chromatographed (silica; EtOAc) to afford the title compound as a white foam (3.5 g). δH ($CDCl_3$) (approximately a 1:1 mixture of diasterioisomers and 1.5:1 ratio of rotamers) 7.13–7.04 (1H, m), 6.70–6.60 (3H, m), 4.89–4.61 (4H, br m), 4.52 and 4.41 (1H, d's, J 14 Hz), 3.72, 3.70 and 3.68 (3H, s's), 3.44–2.84 (4H, br m's), 2.16, 2.15, 1.89 and 1.84 (3H, s's); m/z (ES+, 60V) 353 ($MH^+$).

Intermediate 3

(O-2,6-Dichlorobenzyl)-DL-m-tyrosine methyl ester

Sodium hydride (60% dispersion, 0.27 g, 6.7 mmol) was added to a solution of DL-m-tyrosine methyl ester (1.18 g, 6.1 mmol) and 2,6-dichlorobenzyl bromide (1.45 g, 60 mmol) in DMF (30 ml) at 0°. The reaction was stirred for 2.5 h at room temperature then quenched with water (5 ml) and the solvent evaporated in vacuo. The residue was partitioned between EtOAc (100 ml), and water (50 ml). The organic layer was washed with water (2×50 ml), dried ($MgSO_4$) and the solvent evaporated in vacuo. Chromatography ($SiO_2$ EtOAc/Hexane 4:1) gave the title compound as a gum (1.39 g, 65%). δH ($CDCl_3$); 7.38–7.21 (4H, m), 6.93–6.82 (3H, m), 5.26 (2H, s), 3.77–3.72 (1H, m), 3.72 (3H, s) and 2.83 (1H, dd, 1 8.0, 13.5 Hz); m/z (ESI, 60V). 354 ($M^+$+1).

EXAMPLE 1

N-Acetyl-D-thioproline-(3-amino)-DL-phenylalanine ethyl ester

A solution of Intermediate 2a) (2.00 g, 5.06 mmol) and tin (II) chloride dihydrate (5.72 g, 25.32 mmol) in ethanol (24 ml) was stirred at room temperature for 24 h. The ethanol was then removed in vacuo and the residue partitoned between DCM (10 ml) and saturated aqueous $Na_2CO_3$ (100 ml). The solid precipitate formed was removed by filtration and the phases separated. The aqueous phase was extracted with DCM (2×50 ml) and the combined organics dried ($Na_2SO_4$) and evaporated in vacuo to leave the title compound as a cream foam (1.70 g, 95%). δH ($CDCl_3$) 7.12–6.80 (2H, m) and 6.72–6.32 (3H, m) together (5H, 4×ArH+NH), 5.08–4.98 (1H,m ), and 4.77–4.36 (3H, m), together (4H, 2×CHα+$NCH_2S$), 4.20–4.07 (2H, m, $OCH_2CH_3$), 3.44–2.89 (4H, m, $CH_2Ar+CHCH_2S$), 2.01 (s) and 2.06 (s) and 2.08 (2) and 2.14 (s) together (3H, $CH_3CO$) and 1.27–1.21 (3H, m, $OCH_2CH_3$); m/z (ESI, 60V) 366 ($M^+$+1).

EXAMPLE 2 a) N-Acetyl-D-thioproline-3-[(2,6-dichloroisonicotinoyl)amino]-DL-phenylalanine ethyl ester To a solution of the compound of Example 1 (500 mg, 1.36 mmol) and NMM (0.166 μl, 1.50 mmol) in DCM (20 ml) was added a solution of 2,6-dichloroisonicotinoyl chloride (316 mg, 1.50 mmol) in DCM (2 ml). The solution was stirred for 2 h at room temperature. The reaction mixture was then diluted with DCM (50 ml) and washed with water (2×25 ml) and brine (25 ml) dried and evaporated in vacuo. The residue was purified by chromatography ($SiO_2$, DCM/MeOH, 95:5) to give the title compound as a light brown foam (400 mg, 56%). δH ($CDCl_3$) 9.51 (s) and 9.22 (s) and 8.97 (s) and 8.81 (s) together (1H. NH), 8.50 (2H, s, 2×$ArCl_2H$), 7.91–7.84 (1H, m, ArH), 7.27–7.22 (1H, m, ArH), 7.08–7.11 (1H, m, NH), 6.84–6.89 (1H, m, ArH), 6.72–6.77 (1H, m, ArH), 5.06–4.42 (4H, m, 2×CHα+$NCH_2S$), 4.23–4.11 (2H, m, $OCH_2CH_3$), 3.36–3.00 (4H, m, $CH_2Ar+CHCH_2S$), 2.06 (s) and 2.01 (s) and 1.91 (s) and 1.88 (s) together (3H, $CH_3CO$) and 1.32–1.23 (3H, m, $OCH_2CH_3$); m/z (ESI, 60V) 539 ($M^+$+1).

The following compound was prepared in a similar manner:

b) N-Acetyl-D-thioproline-3-[(4-methoxyphenylacetyl)amino]-DL-phenylalanine ethyl ester
from the compound of Example 1 and 4-methoxyphenylacetyl chloride to yield the title compound as a white foam. δH ($CDCl_3$) (mixture of rotameric and diastereomeric species) 8.06 (s) and 8.00 (s) together (1H. CONH), 7.67 (1H, t, J 8.3 Hz, CONH), 7.3–6.7 (8H, m, ArH), 5.10 (dd) and 4.95 (dd, J 7.0, 3.7 Hz) and 4.8–4.3 (m) together (4H, 2×CHα+$NCH_2S$), 4.2–4.1 (2H, m, $CO_2CH_2CH_3$), 3.80 (3H, s, OMe), 3.64 (s) and 3.62 (s) together (2H, $COCH_2Ar$), 3.4–3.0 (4H, m, $CHCH_2Ar+CHCH_2S$), 2.11 (s) and 2.07 (s) together (3H, $NCOCH_3$), 1.29–1.22 (3H, m, $CO_2CH_2CH_3$) and 1.29–1.22 (3H, m, $CO_2CH_2CH_3$); m/z ($ES^+$, 60V) 514 ($M^+$+H).

EXAMPLE 3 a) N-Acetyl-D-thioproline-3-[(2,6-dichloroisonicotinoyl)amino]-DL-phenylalanine

The compound of Example 2a) (400 mg, 0.74 mmol) was dissolved in a mixture of THF (5 ml) and water (5 ml). Lithium hydroxide monohydrate (34 mg, 0.82 mmol) was added and the mixture stirred at room temperature for 2 h. The THF was removed under reduced pressure and the aqueous residue acidified with aqueous HCl (1M, 2 ml) and the precipitate formed extracted into DCM/MeOH (20 ml, 95:5). The organics were separated, dried and evaporated in vacuo. The solid obtained was dried under reduced pressure at 50° to give the title compound (230 mg, 61%), δH (DMSO-$d^6$, 400K) 10.36 (1H, br s, NH), 8.69 (2H, s, 2×$ArCl_2H$), 7.75–7.63 (1H, m, NH), 7.50 (2H, br s, 2×ArH), 7.27 (1H, dd, J 8.5, 7.5 Hz, ArH), 7.05 (1H, d, J 7.5 Hz, ArH), 4.83–4.73 (2H, m) and 4.62–4.52 (1H, m) and 4.38–4.34 (1H, m) together 4H, 2×CHα+$NCH_2S$, 3.321–2.95 (4H, m, $CH_2Ar+CHCH_2S$), and 1.99 (s) and 1.95 (s) together (3H, $CH_3CO$); m/z (ESI, 60V) 512 ($M^+$+1).

The following compound was prepared in a similar manner:

b) N-Acetyl-D-thioproline-3-[(4-methoxyphenylacetyl)amino]-DL-phenylalanine
from the compound of Example 2b) to yield the title compound as a pale cream powder. δH (DMSO-$d_6$) (mixture of rotameric and diastereomeric species ) 10.02 (s) and 10.00 (s) together (1H, CONH), 8.47 (d, J 8.0 Hz and 8.19 (d, J 8.5 Hz) together (1H, CONH), 7.49–7.39 (2H, m, ArH), 7.25–7.16 (3H, m, ArH), 6.91–6.86 (3H, m, ArH), 4.79–4.66 (2H, m), and 4.44–4.18 (2H, m), together (2×CHα+$NCH_2S$), 3.73 (3H, s, OMe), 3.54 (2H, s, $COCH_2Ar$), 3.17–2.74 (4H, m, $CHCH_2AR+CHCH_2S$), 2.04 (s) and 1.83 (s) together (3H, $COCH_3$); m/z ($ES^+$, 60V) 486 ($M^+$+H).

EXAMPLE 4

N-Acetyl-D-thioproline-3[2,6-dichlorophenylacetyl)amino]-DL-phenylalanine ethyl ester To a solution the compound of Example 1 (500 mg, 1.36 mmol) and NMM (166 μl, 1.50 mmol) in DCM (20 ml) was added a solution of 2,6-dichlorophenylacetyl chloride (335 mg, 1.50 mmol) in DCM (2 ml). The solution was stirred for 2 h at room temperature overnight. The reaction mixture was then diluted with DCM (50 ml) and washed with aqueous HCl (1M, 25 ml), water (25 ml) and brine (25 ml), dried and evaporated in vacuo. The residue was purified by chromatography ($SiO_2$, DCM/MeOH, 94:6) to give the title compound as a pale yellow solid (750 mg, 100%). δH ($CDCl_3$) 8.49 (s) and 8.44 (s) together (1H, NH), 7.67–6.78 (8H, m, 7×ArH+NH), 5.07–4.38 (4H, m, 2×CHα+$NCH_2S$), 4.16–3.99 (4H, m, $OCH_2CH_3$+$COCH_2Ar$), 3.36–2.96 (4H, m, $CH_2Ar+CHCH_2S$), 2.10 (s) and 2.01 (s) and 1.91 (s) together (3H, $CH_3CO$) and 1.25–1.21 (3H, m, $OCH_2CH_3$); m/z (ESI, 60V) 554 ($M^+$+1).

EXAMPLE 5

N-Acetyl-D-thioproline-3-[(2,6-dichlorophenylacetyl)amino]-DL-phenylalanine

The compound of Example 4 (750 mg, 1.37 mmol) was dissolved in a mixture of THF (10 ml) and water (10 ml). Lithium hydroxide monohydrate (63 mg, 1.49 mmol) was added and the mixture stirred at room temperature for 1.5 h. The THF was removed under reduced pressure and the aqueous residue acidified with aqueous HCl (1M) and the precipitate formed isolated by filtration and washed with water. The solid was recrystallised from acetonitrile to give the title compound as a white solid (290 mg, 41%). δH (DMSO-$d^6$, 390K) 9.68 (1H, br s, NH), 7.78–7.66 (1H, m, NH), 7.45–7.39 (4H, m, 4×ArH), 7.30 (1H, dd, J 8.9, 7.2 Hz, ArH), 7.18 (1H, dd, J 7.9, 7.6 Hz, ArH), 6.93 (1H, br d, J 7.6 Hz, ArH), 4.82–4.71 (2H, m) and 4.57–4.47 (1H, m) and 4.37–4.34 (1H, m) together (4H, 2×CHα+$NCH_2S$), 4.07

(2H, s, COCH$_2$Ar), 3.30–2.90 (4H, m, CH$_2$Ar+CHCH$_2$S) and 1.98 (s) and 1.95 (s) together (3H, CH$_3$ CO); m/z (ESI, 60V) 525 (M$^+$+1).

EXAMPLE 6

2-Chloronicotinoyl-(O-2,6-dichlorobenzyl)-DL-m-tyrosine methyl ester

EDC (0.30 g, 1.57 mmol) was added to a suspension of Intermediate 3 (0.51 g, 1.43 mmol), 2-chloronicotinic acid (0.23 g, 1.43 mmol), NMM (0.36 ml, 3.15 mmol) and HOBT (0.36 g, 1.50 mmol) in DMF (20 ml). The reaction was stirred for 16 h at room temperature then water (5mI) was added and the mixture evaporated in vacuo. The residue was partitioned between EtOAc (50 ml) and water (50 ml). The organic layer was washed with water (50 ml), dried (MgSO$_4$) and the solvent removed in vacuo. Chromatography (SiO$_2$ EtOAc/Hexane 7:3) gave the title compound as a foam (0.509 g, 72%). δH (CDCl$_3$) 8.45 (1H, dd, J 2.0, 4.8 Hz), 8.06 (1H, dd, J 2.0, 7.6 Hz), 7.37–7.21 (4H, m), 7.0–6.79 (4H, m), 5.23 (2H, s), 5.08 (1H, dd, J 5.8, 13.2 Hz), 3.79 (3H, s) and 3.27 (2H, dd, J 6.0, 13.9 Hz); m/z (ES1, 60V) 493 (M$^+$).

EXAMPLE 7

N-Acetyl-D-thioproline-(O-2,6-dichlorobenzyl)-DL-m-tyrosine methyl ester

EDC (0.53 g, 2.75 mmol) was added to a suspension of Intermediate 3 (0.88 g, 2.5 mmol), NMM (0.61 ml, 5.5 mmol), and N-acetyl-D-thioproline (0.44 g, 2.5 mmol) in DMF (20 ml). The reaction was stirred at room temperature for 16 h, then water (5 ml) was added and the solvent evaporated in vacuo. The residue was parttioned between EtOAc (50 ml) and water (20 ml). The organic layer was washed with water (20 ml), dried (MgSO$_4$) and the solvent removed in vacuo. Chromatography (SiO$_2$, EtOAc/hexane 70:30) gave two diastereoisomers A (0.52 g, 40%) and B (0.52 g, 40%) as foams.

(A) δH (CDCl$_3$) 7.43–6.75 (7H, m), 5.24 (2H, s), 5.04–3.01 (8H, m), 3.75 (3H, s) and 2.06–1.86 (3H, m). m/z (ESI, 60V) 511 (MH$^+$).

(B) δH (CDCl$_3$) 7.38 (7H, m), 5.25 (2H, d, J 3.4 Hz), 5.04–3.09 (8H, m), 3.75 (3H, s) and 2.14–1.75 (3H, m). m/z (ESI, 60V) 511 (MH$^+$1).

EXAMPLE 8

2-Chloronicotinoyl-(O-2,6-dichlorobenzyl)-DL-m-tyrosine

A solution of the compound of Example 6 (0.50 g, 1.0 mmol) in THF (10 ml and water 10 ml), was trated with lithium hydroxide monohydrate (65 mg, 1.5 mmol) and stirred at room temperature for 1 h. The THF was evaporated in vacuo and the mixture acidified to pH 7 with dilute aqueous HCl, then purified by ion exchange chromatography (Dowex 50×4–400, CH$_3$CN/water) to give the title compound as a white solid (0.40 g, 80%). δH (CD$_3$OD); 10.41 (1H, d, J 8.1 Hz), 9.93 (1H, dd, J 1.8, 4.8 Hz), 9.14–8.40 (8H, m), 6.69 (2H, s), 6.13 (1H, m), 5.51 (1H, br s) and 4.69–4.37 (2H, m). m/z (ESI, 60V) 481 (M$^+$).

EXAMPLE 9

N-Acetyl-D-thioproline(O-2,6-dichlorobenzyl)-m-tyrosine

A solution of the compound of Example 7, Isomer A (0.51 g, 1.0 mmol) in THF (10 ml) and water (10 ml) was treated with lithium hydroxide monohydrate (64 mg, 1.5 mmol) and stirred at room temperature for 1 h. The THF was evaporated in vacuo and then the mixture was acidified to pH 7 with dliute aqueous HCl. The mixture was purified by ion exchange chromatography (Dowex resin 50×4–400, MeCN) to give the title compound as a white solid (0.243 g, 47%). δH (DMSO 390K); 7.52–7.39 (3H, m), 7.23–7.18 (1H, m), 6.93–6.85 (3H, m), 5.27 (2H, s), 4.80–4.71 (2H, m), 4.62–4.56 (1H, m), 4.33 (1H, d, J 9.2 Hz), 3.3–2.48 (4H, m) and 1.93 (3H, s). m/z (ESI. 60V), 497 (MH$^+$).

EXAMPLE 10

N-Acetyl-D-thioproline-(O-2,6-dichlorobenzyl)-m-tyrosine

A solution of the compound of Example 7, isomer B (0.51 g, 1.0 mmol) in THF (10 ml) and water (10 ml), was treated with lithium hydroxide monohydrate (64 mg, 1.5 mmol) and stirred at room temperature for 1 h. The THF was evaporated in vacuo and the mixture acidified to pH 7 with dilute aqueous HCl, the aqueous was then passed through a Dowex resin column 50×40. The mixture was purified by ion exchange chromatography (Dowex resin 50×4–400, MeCN) to give the title compound as a white solid (0.37 g, 63%). δH (DMSO 390K) 7.52–7.39 (3H, m), 7.2 (1H, m), 6.92–6.85 (3H, m), 5.27 (2H, s), 4.80–4.71 (2H, m), 4.58–4.53 (1H, m), 4.35 (1H, d, J 8.9 Hz), 3.26–3.11 (2H, m), 3.0–2.92 (2H, m) and 1.93 (3H, s). m/z (ESI, 60V), 497 (M$^+$).

EXAMPLE 11

N-Acetyl-D-thioproline-3-[(trimethylacetyl)amino]-DL-phenylalanine ethyl ester Trimethylacetyl chloride (168 μl, 1.36 mmol) was added to a solution of the compound of Example 1 (450 mg, 1.23 mmol) and NMM (148 μl, 1.36 mmol) in DCM (30 ml). The reaction mixture was stirred for 5 h at room temperature then diluted with DCM (50 ml), washed with dilute HCl(aq) (25 ml), water (2×25 ml) and brine (25 ml), dried and evaporated in vacuo. The residue was purified by column chromatography [SiO$_2$, DCM/MeOH, 97:3] to give the title compound as a white foam (460 mg, 83%). δH (CDCl$_3$) (mixture of rotameric and diastereromeric species observed) 8.20 (s) and 8.10 (s) together (1H, NH), 7.85 (1H, apparent t, J 9.4 Hz, NH), 7.5–6.5 (4H, m, ArH), 5.2–4.1 (6H, m, 2×CHα, NCH$_2$S, CO$_2$CH$_2$CH$_3$), 3.5–3.0 (4H, m, CH$_2$Ar+CHCH$_2$S), 17 (s) and 2.15 (s) together (3H, NCOCH$_3$), 1.32–1.22 (12H, m, CH$_3$CO+CO$_2$CH$_2$CH$_3$); m/z (ES$^+$, 60V) 450 (M$^+$+1).

EXAMPLE 12

N-Acetyl-D-thioproline-3-[(trimethylacetyl)amino]-DL-phenylalanine

The title compound was obtained as a white powder by hydrolysis of the ester of Example 11 using the procedure of Example 3a). δH (DMSO-d$_6$) (mixture of rotameric+diastereomeric species) 9.09 (1H, br s, NH), 8.46 (t, J 8.9 Hz), 8.20 (d, J 8.2 Hz) and 8.09 (d, J 7.7 Hz), together (1H, H), 7.58–7.4 (2H, m, ArH), 7.19–7.12 (1H, m, ArH), 6.92–6.87 (1H, m, ArH), 4.86–4.64 (2H,m) and 4.47–4.19 (2H,m) together (2×CHα+NCH$_2$S), 3.38–2.80 (4H, m, CH$_2$Ar+CHCH$_2$S), 2.08 (s), 2.07 (s), 1.85 (s) and 1.78 (s) together (3H, NCOCH$_3$) and 1.22 (9H, s, Me$_3$CO); m/z (ES$^+$, 60V) 422 (M$^+$+H).

EXAMPLE 13

N-Acetyl-L-thioproline-D,L-O-(1-adamantanecarbonylmethyl)-m-tyrosine methyl ester A mixture of Intermediate 2b) (1.0 g, 2.84 mmol), caesium carbonate (0.926 g, 2.84 mmol) and 1-adamantylbromomethylketone (0.73 g, 2.84 mmol) in dry DMF (30 ml) was stirred at room temperature for 2 h. The volatiles were removed in vacuo and the residue partitioned between EtOAc (100 ml) and 2% aqueous HCl (40 ml). The phases were separated and the aqueous phase re-extracted with EtOAc (2×30 ml). The combined organic extracts were washed with brine (10 ml), dried (MgSO$_4$) and evaporated in vacuo to afford a colourless foam. Purification by chromatography (silica; EtOAc) afforded the title compound as a colourless foam (824 mg, 55%). δH (CDCl$_3$) (approximately a 1:1 mixture of diastereoisomers and 1.5:1 ratio of rotamers) 7.21–7.14 (1H, m), 6.84–6.71 (3H, m),5.01–4.96 (2H, m), 4.93–4.62 (4H, m's), 4.53 and 4.40 (1H, d's, J 14 Hz), 3.74, 3.72 and 3.70 (3H, s's), 3.42–2.83 (4H, br m) and 2.1–1.72 (18H, m's and s's); m/z (ES+, 60V) 551 (MNa+) and 529 (MH+).

EXAMPLE 14

N-Acetyl-L-thioproline-D,L-O-(1-adamantanecarbonylmethyl)-m-tyrosine

The compound of Example 13 (258 mg, 0.49 mmol) was treated with a solution of LiOH.H$_2$O (23 mg, 0.55 mmol) in water (2.5 ml) and dioxane (2.5 ml) at room temperature for 2 h. The reaction mixture was acidified with a few drops of concentrated HCl and the volatiles removed in vacuo. The residue was chromatographed [silica; DCM (200), MeOH (20), AcOH (3), H$_2$O (2)] to afford the product as a colourless oil. Freeze drying from aqueous methanol gave the title compound as a white amorphous solid (240 mg, 96%). δH (CDCl$_3$)(approximately 1:1 mixture of diastereoisomers and 1.5:1 ratio of rotamers) 7.21–7.12 (1H, m, apparent t), 6.88–6.70 (3H, m), 5.0–4.96 (2H, m), 4.90–4.61 (3H, br m), 4.54 and 4.40 (1H, d, J 14 Hz), 3.42–2.85 (4H, m's), 2.12, 2.10, 1.90 and 1.85 (3H, s's), 2.10–2.00 (3H, narrow m) 1.98–1.90 (6H, narrow m) and 1.80–1.76 (6H, narrow m); m/z (ES$^+$, 60V) 537 (MNa$^+$), 515 (MH$^+$).

The following assays can be used to demonstrate the potency and selectivity of the compounds according to the invention. In each of these assays an IC$_{50}$ value was determined for each test compound and represents the concentration of compound necessary to achieve 50% inhibition of cell adhesion where 100%=adhesion assessed in the absence of the test compound and 0%=absorbance in wells that did not receive cells.

$\alpha_4\beta_1$ Integrin-dependent Jurkat Cell Adhesion to VCAM-lg 96 well NUNC plates were coated with F(ab)$_2$ fragment goat anti-human IgG Fcγ-specific antibody [Jackson Immuno Research 109-006-098: 100 µl at 2 µg/ml in 0.1M NaHCO$_3$, pH 8.4], overnight at 40°. The plates were washed (3×) in phosphate-buffered saline (PBS) and then blocked for 1 h in PBS/1% BSA at room temperature on a rocking platform. After washing (3× in PBS) 9 ng/ml of purified 2 d VCAM-lg diluted in PBS/1% BSA was added and the plates left for 60 minutes at room temperature on a rocking platform. The plates were washed (3× in PBS) and the assay then performed at 37° C. for 30 min in a total volume of 200 µl containing 2.5×10$^5$ Jurkat cells in the presence or absence of titrated test compounds.

Each plate was washed (2×) with medium and the adherent cells were fixed with 100 µl methanol for 10 minutes followed by another wash. 100 µl 0.25% Rose Bengal (Sigma R4507) in PBS was added for 5 minutes at room temperature and the plates washed (3×) in PBS. 100 µl 50% (v/v) ethanol in PBS was added and the plates left for 60 min after which the absorbance (570 nm) was measured.

$\alpha_4\beta_7$ Integrin-dependent JY Cell Adhesion to MAdCAM-lg

This assay was performed in the same manner as the $\alpha_4\beta_1$ assay except that MAdCAM-lg (150 ng/ml) was used in place of 2d VCAM-lg and a subline line of the β-lympho blastoid cell-line JY was used in place of Jurkat cells. The IC$_{50}$ value for each test compound was determined as described in the $\alpha_4\beta_1$ integrin assay.

$\alpha_5\beta_1$ Integrin-dependent K562 Cell Adhesion to Fibronectin 96 well tissue culture plates were coated with human plasma fibronectin (Sigma F0895) at 5 µg/ml in phosphate-buffered saline (PBS) for 2 hr at 37° C. The plates were washed (3× in PBS) and then blocked for 1 h in 100 µl PBS/1% BSA at room temperature on a rocking platform. The blocked plates were washed (3× in PBS) and the assay then performed at 37° C. in a total volume of 200 µl containing 2.5×10$^5$ K562 cells, phorbol-12-myristate-13-acetate at 10 ng/ml, and in the presence or absence of titrated test compounds. Incubation time was 30 minutes. Each plate was fixed and stained as described in the $\alpha_4\beta_1$ assay above.

$\alpha_m\beta_2$-dependent Human Polymorphonuclear Neutrophils Adhesion to Plastic 96 well tissue culture plates were coated with RPMI 1640/10% FCS for 2 h at 37° C. 2×10$^5$ freshly isolated human venous polymorphonuclear neutrophils (PMN) were added to the wells in a total volume of 200 µl in the presence of 10 ng/ml phorbol-12-myristate-13-acetate, and in the presence or absence of test compounds, and incubated for 20 min at 37° C. followed by 30 min at room temperature. The plates were washed in medium and 100 µl 0.1% (w/v) HMB (hexadecyl trimethyl ammonium bromide, Sigma H5882) in 0.05M potassium phosphate buffer, pH 6.0 added to each well. The plates were then left on a rocker at room temperature for 60 min. Endogenous peroxidase activity was then assessed using tetramethyl benzidine (TMB) as follows: PMN lysate samples mixed with 0.22% H$_2$O$_2$ (Sigma) and 50 µg/ml TMB (Boehringer Mannheim) in 0.1M sodium acetate/citrate buffer, pH 6.0 and absorbance measured at 630 nm.

αIIb/β$_3$-dependent Human Platelet Aggregation

Human platelet aggregation was assessed using impedance aggregation on the Chronolog Whole Blood Lumiaggregometer. Human platelet-rich plasma (PRP) was obtained by spinning fresh human venous blood anticoagulated with 0.38% (v/v) tri-sodium citrate at 220×g for 10 min and diluted to a cell density of 6×10$^8$/ml in autologous plasma. Cuvettes contained equal volumes of PRP and filtered Tyrode's buffer (g/liter: NaCl 8.0; MgCl$_2$.H$_2$O 0.427; CaCl$_2$ 0.2; KCl 0.2; D-glucose 1.0; NaHCO$_3$ 1.0; NaHPO$_4$.2H$_2$O 0.065). Aggregation was monitored following addition of 2.5 µM ADP (Sigma) in the presence or absence of inhibitors.

In the above assays the compounds of the invention, for example compounds of the Examples generally have IC$_{50}$ values in the $\alpha_4\beta_1$ and $\alpha_4\beta_7$ assays of 1 µM and below. In the other assays featuring α integrins of other subgroups the same compounds had IC$_{50}$ values of 50 µM and above thus demonstrating the potency and selectivity of their action against $\alpha_4$ integrins.

What is claimed is:

1. A compound of formula (1):

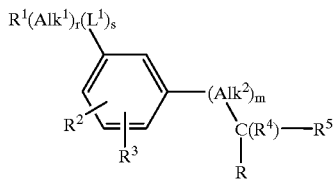

wherein
- $R^1$ is an optionally substituted aromatic or heteroaromatic group;
- $Alk^1$ is an optionally substituted aliphatic or heteroaliphatic chain;
- $L^1$ is a linker atom or group selected from —O—, —S—, —C(O)—, —C(O)O—, —C(S)—, —S(O)—, —S(O)$_2$—, —N(R$^8$)—, —CON(R$^8$)—, —OC(O)N(R$^8$)—, —CSN(R$^8$)—, —N(R$^8$)C(O)—, —N(R$^8$)C(O)O—, —N(R$^8$)CS—, —S(O)$_2$N(R$^8$)—, —N(R$^8$)S(O)$_3$—, —N(R$^8$)CSN(R$^8$)—, and —N(R$^8$)SO$_2$N(R$^8$)— (wherein R$^8$ may be the same or different and is a hydrogen atom or an optionally substituted straight or branched alkyl group);
- r and s is each zero or an integer 1;
- $R^2$ and $R^3$, which may be the same or different, is each a hydrogen or halogen atom, a hydroxyl or nitro group, or a straight or branched alkyl, haloalkyl, alkoxy, or haloalkoxy group;
- $Alk^2$ is a straight or branched alkylene chain;
- m is zero or an integer 1;
- $R^4$ is a hydrogen atom or a methyl group;
- $R^5$ is a group —L$^2$(CH$_2$)$_t$R$^6$ in which L$^2$ is a —N(R$^7$)CO— (where R$^7$ is a hydrogen atom or a straight or branched alkyl group) or —N(R$^7$)CS— group, t is zero or the integer 1, and R$^6$ is an optionally substituted pyrrolidinyl, thiazolidinyl, phenyl or pyridyl group;
- R is a carboxylic acid; provided that:
  - (1) when $R^1$ is phenyl, r and s are each zero, $R^2$ and $R^3$ are hydrogen, $Alk^2$ is CH$_2$, m is 1, $R^4$ is hydrogen, R is CO$_2$H, and L$^2$ is —N(CH$_3$)C(O)—, then R$^5$ is other than substituted phenyl; and
  - (2) when r is zero and s is 1, L$^1$ is other than —CON(R$^8$)—;

or a pharmaceutically acceptable salt, solvate, or hydrate thereof.

2. A compound according to claim 1 wherein $Alk^2$ is —CH$_2$— and m is the integer 1.

3. A compound according to claim 1 wherein $R^4$ is a hydrogen atom.

4. A compound according to claim 1 wherein -(Alk$^1$)$_r$(L$^1$)$_s$ is —CH$_2$O— or —CON(R$^8$)—.

5. A compound according to claim 4 wherein (Alk$^1$)$_r$(L$^1$)$_s$ is —CONH—.

6. A compound according to claim 1 wherein $R^1$ is an optionally substituted phenyl, pyridyl or pyrimidinyl group.

7. A compound according to claim 1 wherein $R^5$ is a —NHCOR$^6$ or —NHCSR$^6$ group.

8. A compound which is:

N-Acetyl-D-thioproline-3-[(2,6-dichloroisonicotinoyl)amino]-DL-phenylalanine;
N-Acetyl-D-thioproline-3-[(4-methoxyphenylacetyl)amino]-DL-phenylalanine;
N-Acetyl-D-thioproline-3-[(2,6-dichlorophenylacetyl)amino]-DL-phenylalanine;
2-Chloronicotinoyl-(0,2,6-dichlorobenzyl)-DL-m-tyrosine;
or a pharmaceutically acceptable salt, solvate or hydrate thereof.

9. A pharmaceutical composition comprising a compound according to claim 1 and one or more pharmaceutically acceptable carriers, excipients or diluents.

* * * * *